United States Patent [19]

Komiya et al.

[11] Patent Number: 5,504,068
[45] Date of Patent: Apr. 2, 1996

[54] TOPICAL PREPARATIONS CONTAINING CYCLOSPORIN

[75] Inventors: Katsuo Komiya, Tokyo; Rie Igarashi; Mitsuko Takenaga, both of Kawasaki; Akira Yanagawa, Yokohama; Yutaka Mizushima; Tateo Nishimura, both of Tokyo; Toshitaka Kudo, Yokohama; Kunio Ando, Kawasaki, all of Japan

[73] Assignee: LTT Institute Co., Ltd., Japan

[21] Appl. No.: 975,548

[22] PCT Filed: Jun. 22, 1992

[86] PCT No.: PCT/JP92/00798

§ 371 Date: Feb. 23, 1993

§ 102(e) Date: Feb. 23, 1993

[87] PCT Pub. No.: WO93/00106

PCT Pub. Date: Jan. 7, 1993

[30] Foreign Application Priority Data

Jun. 27, 1991 [JP] Japan ................... 3-252696
Jan. 17, 1992 [JP] Japan ................... 4-027396
Mar. 10, 1992 [JP] Japan ................... 4-108089

[51] Int. Cl.⁶ ............................................. A61K 38/13
[52] U.S. Cl. ................................. 514/11; 514/885
[58] Field of Search ............................. 514/885, 886, 514/887, 11

[56] References Cited

U.S. PATENT DOCUMENTS

4,996,193  2/1991  Hewitt et al. ............................. 514/11

FOREIGN PATENT DOCUMENTS

4005190  8/1990  Germany.
2218334  11/1989  United Kingdom.
2222770  3/1990  United Kingdom.
2228198  8/1990  United Kingdom.

*Primary Examiner*—Marianne M. Cintins
*Assistant Examiner*—P. G. Spivack
*Attorney, Agent, or Firm*—Lorusso & Loud

[57] ABSTRACT

A topical preparation containing cyclosporin as an active ingredient, is disclosed that contains (a) cyclosporin; (b) an organic solvent for dissolving the cyclosporin; (c) an ester of a fatty acid with a monovalent alcohol having a total number of carbon atoms of 8 or more and/or an alkanol amine, each being in liquid state at 25°C; (d) an oily substance in solid state at 25°C; and (e) a surfactant. The cyclosporin is present in a concentration ranging from appoximately 0.1% to 10% by weight and the ester and/or alkanol amine are/is present in a concentration ranging from approximately 1% to 15% by weight. The topical preparations are active against atopic dermatitis, psoriasis and allergic contact dermatitis.

19 Claims, No Drawings

TOPICAL PREPARATIONS CONTAINING CYCLOSPORIN

TECHNICAL FIELD

The present invention relates to topical preparations containing cyclosporin as a major active component. The topical preparations containing cyclosporin include topical preparations in the form of an emulsion or a non-emulsion.

The term "cyclosporin" referred to in this application is intended to mean a single substance or a mixture of a group of cyclosporin antibiotics which are described in detail in Japanese Patent Laid-open Publication (kokai) No. 2-17,127.

BACKGROUND ART

Cyclosporin is known as an immune inhibitor and it has extensively been employed in the field of the transplant of organs including the kidney. Recently, cyclosporin becomes apparent as being effective to various diseases that are caused mainly from autoimmune reaction, in addition to the efficacy for the transplant of the organs. A number of literature has already been published which reports the efficacy of cyclosporin forarthritis. Autoimmune diseases to which cyclosporin has been applied or proposed to be applied may include, for example, autoimmune blood diseases, chronic bronchial asthma, systemic erythematosus, polymyositis, systemic scleroderma, Wegner syndrome, myasthenia gravis, psoriasis vulgaris, autoimmune intestinal diseases (idiopathic ulcerative colitis, Crohn disease), sarcoidosis, multiple sclerosis, juvenile diabetes mellitus, uveitis, psoriatic rheumatoid, glomerulonephritis, and the like.

As described hereinabove, cyclosporin contributes largely to the inhibition of rejection at the time of transplanting organs and autoimmune therapy; however, it is also known that it may often cause severely adverse affect upon the kidney when administered orally over a long period of time so that this toxicity to the kidney has been the cause of suppressing cyclosporin from being extensively employed. It can be noted that there are many cases where morbid states are caused to occur at the skin, eye or joint to which topical preparations can be applied. In the case of diseases that can be administered with topical preparations, it is advantageous to avoid systemic administration that might cause disturbances to occur in the kidney. If the focus of a disease is restricted to a layer of the dermis, topical administration through the epidermis is more advantageous than other ways of administration because it can save the amount of a medicine to be administered and further the efficacy of the medicine can be enhanced in association with a local rise in the concentration of the medicine, while systemic side effects can be reduced. The way of administration in the form of topical preparations can be said to be one of the most effective drug delivery systems (DDS) for cyclosporin.

On the other hand, it is extremely difficult to formulate cyclosporin into topical preparations so as to maintain its highly therapeutical effect, unlike watersoluble or low-molecular weight, pharmaceutically effective substances. One of the reasons for this difficulty is because the cyclosporin is a large cyclopolypeptide having a molecular weight of larger than 1,200 so that it suffers from the difficulty in allowing cyclosporin to infuse or penetrate through the horny skin layer into the focal site present in the dermis layer. Another reason for the difficulty is because the cyclosporin is insoluble in water and there is the restriction upon the kind of organic solvents in which the cyclosporin can be dissolved. As such specific organic solvents, a lower alkanol such as ethanol or isopropanol may be generally employed. However, such a lower alkanol is too highly irritative to the skin when it is employed for topical preparations in a relatively high concentration, so that safe topical preparations cannot be provided. On the other hand, when the lower alcohol is employed in a relatively low concentration for topical preparations, the ability of the cyclosporin to be dispersed uniformly in the topical preparations may be impaired, thereby providing no topical preparations with a highly therapeutical effect.

Reports on clinical research of cyclosporin ointments have been published to the effect that a 10% cyclosporin formulation may be pharmaceutically effective or ineffective, so that its pharmaceutical effects may or may not be reproduced. Some reports describe specific compositions of cyclosporin formulations yet no clear pharmaceutical effects therefor are described.

For example, Japanese Patent Laid-open Publication No. 2-17,127 discloses compositions which contain, as essential components, cyclosporin and a mono- or polyunsaturated fatty acid or an unsaturated alcohol, each having from 12 to 24 carbon atoms. The mono- and polyunsaturated fatty acids may include, for example, vaccenic acid, linoleic acid, linolenic acid, elaidic acid, erucic acid, and the like. The unsaturated alcohol may include, for example, vaccenyl alcohol, linoleyl alcohol, linolenyl alcohol, elaidyl alcohol, erucyl alcohol, and the like. Further, it describes the compositions are effective to various skin diseases; however, that publication does not specify its pharmaceutical effects and refers merely to the ability of the cyclosporin to infuse or penetrate through the skin and to the concentration of the cyclosporin. The publication is thoroughly silent about the extent, for example, to which the cyclosporin is effective against psoriatic diseases.

Several cases of skin diseases are reported; many of the literature states that cyclosporin is effective against the skin diseases.

For example, atopic dermatitis is reported in Acta. Derm. Venerol.: Suppl. 144, 136–138 (1989) where an alcoholic oily gel of containing cyclosporin at the rate of 10% by weight is effective against atopic dermatitis. Further, Arch. Derm.: 125, p. 570 (1989) reports that an alcoholic oily gel of a 10% (by weight) cyclosporin is effective.

There are reports of contact-type dermatitis, for example, in Arch. Dermato-1: 125, 568 (1989) which reports to the effect that cyclosporin is employed for a human DNCB test with no effect. Further, Contact Dermatitis: 19, 129–132 (1988) makes a review on three formulations: a 10% cyclosporin formulation in Labrafil (polyoxyl-5-oleate, olive oil and ethanol), a 5% cyclosporin formulation in castor oil, and a 5% cyclosporin formulation in castor oil containing 20% propylene glycol; however, it states the results of this review are not so satisfactory that a more effective solvent is required. In addition, Contact Dermatitis, 20, 155–156 states that none of three formulations, or 0.1%, 1% and 10% cyclosporin formulations, are effective at all against contact dermatitis.

Pharmaceutical effect of cyclosporin upon psoriasis is described, for example, in Clin. Res., 34, 1007A (1986), in which it is described that topical administration of cyclosporin is not effective for the therapy to psoriasis, although neither the concentration of cyclosporin nor the composition thereof are specified. It is also described in Lancet, 1, 806 (1987) that a 2% by weight cyclosporin (on ointment base) is as effective upon psoriasis as placebo.

Further, J. Amer. Acad. Dermatol., 18, 378–379 (1988) describes that a 5% cyclosporin solution in olive oil is equal to the sole use of olive oil that is employed as the base in the previous case. In addition, J. Amer. Acad. Dermatol., 22, 126–127 (1990) states that a gel comprising 10% cyclosporin, 43% olive oil, 10% ethanol, 30% polyoxyl-5-oleate and 7% colloidal silica did not produce any effect upon psoriasis. Furthermore, it is reported in Brit. J. Derm., 122, 113–114 (1990) that a 5% (by weight) cyclosporin ointment was not effective.

Reports on alopecia areata are made, for example, in Lancet, 2, 803–804 (1986) where it is described that a 2% cyclosporin oily solution was effective. In addition, Lancet, 2, 971–972 (1986) reports that a 5% (wc) cyclosporin formulation in oil was effective against alopecia areata. On the other hand, Acta. Derm. Venereol., 69, 252–253 (1989) describes that a 10% cyclosporin oily preparation was not effective. Furthermore, J. Amer. Acad. Dermatol., 22, 251–253 (1989) reports that a 5% cyclosporin formulation was effective against male alopecia, although no specific compositions are described therein.

As long as literature as described hereinabove has been reviewed, it is considerably difficult to draw a conclusion that cyclosporin is topically effective against the skin diseases as specified hereinabove. Even if it could be said that cyclosporin would be effective against the skin diseases, it can be said that cyclosporin should be employed in a considerably large amount. If cyclosporin preparations are not topically effective against the skin diseases or the effect is not satisfactory, it can be said in many occasions that the kinds of formulation components and the dosage are inappropriate. In summary, no conventional topical cyclosporin preparations can achieve the object to utilize cyclosporin effectively as topical preparations.

DISCLOSURE OF INVENTION

The primary object of the present invention is to provide a topical preparation containing cyclosporin, which acts effectively upon skin diseases, is useful therefor, and is highly safe.

Another object of the present invention is to provide a topical preparation containing cyclosporin, which is lower in the concentration of a lower alcohol and high in safety.

A further object of the present invention is to provide a highly safe topical preparation containing cyclosporin, which does not yet contain any quantity of a lower alcohol.

As a result of extensive research and reviews on cyclosporin-containing topical preparations which are superior in the ability of infusion or penetration through the skin or the horny skin layer yet which are less in irritation to the skin and high in safety, the present invention has been completed on the basis of the new finding as will be described hereinafter.

One aspect of the present invention provides the topical preparation containing cyclosporin, which is characterized by (a) cyclosporin; (b) an organic solvent in which the cyclosporin is to be dissolved; (c) an ester of an fatty acid with a monovalent alcohol, which is in liquid state at 25° C. and which has a total number of carbon atoms of 8 or more, and/or an alkanol amine in liquid form at 25° C.; (d) an oily substance in a solid form at 25° C.; and (e) a surfactant, wherein an amount of the cyclosporin ranges from 0.1% by weight to 10% by weight and a total amount of the ester of the fatty acid with the monovalent alcohol and/or the alkanol amine ranges from 1% by weight to 15% by weight.

Another aspect of the present invention provides a topical preparation containing cyclosporin, which is characterized by (a) cyclosporin; (b) a lower alcohol; (c) an fatty acid ester in liquid state at 25° C. and/or an alkanol amine in liquid state at 25° C.; (d) an oily substance in solid state at 25° C.; and (e) a surfactant, wherein an amount of the cyclosporin ranges from 0.1% by weight to 10% by weight, an amount of the lower alcohol ranges from 2% by weight to 15% by weight; and a total amount of the fatty acid ester and/or the alkanol amine ranges from 1% by weight to 15% by weight.

The cyclosporin-containing topical preparations according to the present invention are characterized by the features that the compositions are different from those of the conventional cyclosporin topical preparations as reported in the aforesaid literature and it can achieve the objects of the present invention in an effective way by using a reduced amount of cyclosporin.

The topical preparations containing cyclosporin according to the present invention is provided with the features as follows:

1. They are superior in therapeutic effect;
2. They are highly stable (i.e., cyclosporin does not become free from the topical preparations, no crystallization of cyclosporin is caused to occur, and no chemical reaction of cyclosporin is caused to occur with any other components of the compositions);
3. They are easily administered topically;
4. They contain cyclosporin in a highly uniformly dispersed state; and
5. They are highly safe.

In order to determine the formulations of the topical preparations according to the present invention, the selection of each component of the formulation and the rates of the components are of significant factors. For example, when the topical preparations are employed in the form of ointment, the pharmaceutical effect of the ointment, the biological activity of the ointment, and the physicochemical stability of the ointment should be taken into account. Heretofore, in usual cases, a higher saturated fatty acid or an fatty acid such as oleic acid or 12-hydroxystearic acid has been employed as an ointment base. Among those fatty acids, lauric acid, myristic acid, palmitic acid and stearic acid have been employed to form soap, together with an alkali, particularly potassium hydroxide, which in turn helps emulsify the formulated medicine.

It should be noted herein, however, that the fatty acid, whether it is employed as it is or in the form of potassium soap as an ointment base, for the cyclosporin-containing topical preparations according to the present invention, is little effective for emulsifying cyclosporin in the topical preparations, whereby no topical preparations with an highly pharmaceutical effect can be provided, and the stability of ointment may be impaired.

BEST MODES FOR CARRYING OUT THE INVENTION

The topical preparations according to the present invention contains cyclosporin, as a major active component, at a rate ranging from 0.1% to 10% by weight, preferably from 1% by weight to 7% by weight. It is to be noted herein that the topical preparations of the present invention can demonstrate highly therapeutic effects in such a low concentration.

The topical preparations according to the present invention contains the organic solvent for cyclosporin, which is in liquid state at ambient temperature (25° C.) and which can dissolve the cyclosporin. Such organic solvents may include an aliphatic alcohol and a fatty acid ester with a polyvalent alcohol.

As the aliphatic alcohols, there may be employed any lower alcohol and higher alcohol as long as they are liquid at ambient temperature. The alcohol may be a straight or branched one or may be saturated or unsaturated one. Specific examples of such aliphatic alcohols may include a lower alcohol such as ethanol, propanol, isopropanol, butanol, and the like, and a higher alcohol such as octyl alcohol, nonyl alcohol, decyl alcohol, 2-octyl dodecanol, 2,6-dimethyl-4-heptanol, oleyl alcohol, and the like. The branched higher alcohol is preferably appropriate as the organic solvent for the cyclosporin.

The polyvalent alcohol-fatty acid ester may be represented by the following formula:

where

R$^1$ is an alkyl group having from 4 to 12 carbon atoms, preferably from 6 to 10 carbon atoms; and R$^2$ is an alkyl group having from 2 to 4 carbon atoms.

Specific examples of the polyvalent alcohol-fatty acid ester may include, for example, propylene glycol caprylate, propylene glycol caprate, butylene glycol caprylate, butylene glycol caprate, glycol butyrate, and propylene glycol butyrate.

The organic solvents as described hereinabove may be employed solely or in admixture with the other organic solvents. The mixture advantageously contains the lower alcohol in the range from approximately 5% to 60% by weight, preferably from approximately 10% to 50% by weight.

The organic solvents may be admixed with the cyclosporin at the rate ranging from approximately 0.5 part to 10 parts by weight, preferably from approximately 1 part to 5 parts by weight, per part by weight of cyclosporin. As the organic solvents, the lower alcohol, particularly ethanol, is preferred. The lower alcohol can serve as a solvent for the cyclosporin as well as acts for accelerating the ability of the cyclosporin to infuse or penetrate through the skin.

The rate of the lower alcohol to be admixed with the cyclosporin may preferably be determined so as to amount to 2% by weight or more with respect to the total weight of the topical preparation, in order to accelerate the ability of the cyclosporin for infusion or penetration through the skin. If the concentration of the lower alcohol increases, the extent of irritation becomes so severer that the concentration of the lower alcohol may be reduced to 15% by weight or lower with respect to the total weight of the topical preparation. It is to be noted, however, that the concentration of the lower alcohol may preferably range from 3% to 6% by weight with respect to the total weight of the topical preparation, in order to focus on improvements in the ability of the cyclosporin for infusion or penetration through the skin and a low degree of irritation.

It is noted that for the topical preparations according to the present invention, it is preferred to use such an organic solvent as having a boiling point of 160° C. or higher, preferably 180° C. or higher and being sparingly volatile or volatilizable. Such organic solvents may include, for example, a higher aliphatic alcohol having 8 carbon atoms or more and a divalent alcohol-fatty acid ester.

The topical preparations according to the present invention contains the ester of the fatty acid in liquid state at ambient temperature with the monovalent alcohol and/or the alkanol amine. The fatty acid ester with the monovalent alcohol may have 8 carbon atoms or more, preferably 12 carbon atoms or more.

The monovalent alcohol component of the monovalent alcohol-fatty acid esters may be a residue of a straight- or branch-chained aliphatic alcohol having from 1 to 22 carbon atoms, preferably from 2 to 18 carbon atoms. The fatty acid component may be a straight-chained or branch-chained, monovalent or divalent fatty acid having from 4 to 22 carbon atoms, preferably from 6 to 18 carbon atoms. The monovalent alcohol and fatty acid components may in each case contain an unsaturated bond. The monovalent alcohol component thereof may include, for example, ethanol, propanol, isopropanol, butanol, hexanol, octanol, isooctanol, dodecanol, isododecanol, myristyl alcohol, cetyl alcohol, hexadecyl alcohol, 2-ethylhexyl alcohol, 2-octyl dodecanol and the like. The fatty acid component may include, for example, a monovalent fatty acid such as butyric acid, octanoic acid, nonanoic acid, caprylic acid, capric acid, myristic acid, palmitic acid, stearic acid, linoleic acid, linolic acid, and erucic acid, and a divalent fatty acid such as succinic acid, adipic acid, pimelic acid, suberic acid, azelaic acid, sebacic acid, and dodecane diacid. Preferred examples of the fatty acid esters with the monovalent alcohols may include, for example, a monovalent fatty acid ester such as ethyl myristate, isopropyl myristate, isotridecyl myristate, isopropyl laurate, isopropyl caprylate, isopropyl palmirate, isopropyl butyrate, amyl butyrate, and octyl butyrate, and a divalent fatty acid ester such as diethyl succinate, diisopropyl succinate, diethyl adipate, diisopropyl adipate, diisooctyl adipate, dioctyl adipate, didecyl adipate, decyl isooctyl adipate, diethyl azelate, diisopropyl azelate, diisooctyl azelate, diethyl sebacate, diisopropyl sebacate, dibutyl sebacate, and dioctyl sebacate.

Specific examples of the alkanol amines may include, for example, diethanoi amine, triethanol amine, isopropanol amine, triisopropanol amine, dibutanol amine, tributanol amine, and the like.

The monovalent alcohol-fatty acid ester and the alkanol amine can serve as improving the ability of the cyclosporin solution in the organic solvents to infuse or penetrate through the skin as well as demonstrate the action of homogeneously dispersing the cyclosporin, dissolved in the organic solvents, in the oily substance in solid form. The rate of these compounds may range usually from approximately 1% to 15% by weight, preferably from approximately 3% to 10% by weight, with respect to the total weight of the topical preparation. Further, these compounds may be employed at the rate ranging usually from approximately 2 parts to 5 parts by weight, preferably from approximately 2.5 parts to 4 parts by weight, with respect to part by weight of the organic solvent or solvents.

The topical preparations according to the present invention contains the oily substance in solid form at ambient temperature. It is noted herein that the term "solid" referred to herein is intended to mean semisolid as well as solid. The oily substances may include, for example, an alcohol, an fatty acid, an ester, a triglyceride, wax, vaseline, and the like. The alcohol may include, for example, palmityl alcohol, stearyl alcohol, eicosyl alcohol, glycerine, polyglycerin, and the like. The fatty acid may include, for example, palmitic acid, stearic acid, oleic acid, arachic acid, behenic acid, montanic acid, melissic acid, sebacic acid, and the like. The ester may include, for example, butyl stearate, hexyl laurate, myristyl myristate, dodecyl oleate, 2-octyldodecyl myristate, hexyl decyl octanoate, cetyl lactate, glyceryl caprate, glyceryl caprilate, and the like. As the triglyceride, there may be employed a variety of materials originating from sources such as animals or naturally occurring plants or vegetables, which are generally called fats and oils and which can be commercially available. It may include, for example, a large variety of vegetable oils, cow fats, liver fats, lanolin, lard, and the like. Preferable ones are vegetable oils, particularly olive oil, camellia oil, soybean oil, rapeseed oil, corn oil, castor oil, safflower oil, and the like. There may also be employed fish oil rich in eicosapentadecanoic acid that recently draws increasing attention due to its action for allergy or malignant tumor.

The rate of the oily substance is not restricted to a particular one and may be formulated at any arbitrary rate in accordance with the desired properties of the topical preparations. Generally, the rate of the oily substance may range from approximately 1 part to 10 parts by weight, preferably from approximately 2 parts to 8 parts by weight, with respect to part by weight of the total weight of the organic solvent and the monovalent alcohol-fatty acid ester and/or the alkanol amine, which is in liquid state at room temperature.

The surfactant is contained in the topical preparations according to the present invention. As the surfactants, there may be employed a variety of surfactants, including anionic, cationic, non-ionic or amphoteric ones. The non-ionic surfactants may preferably be employed in terms of a low degree of irritation to the skin. As the non-ionic surfactants, there may be mentioned, for example, an ethylene oxide type surfactant, a polyhydroxy type surfactant, a polymer type surfactant, and the like. The ethylene oxide type surfactants may include, for example, an ethylene oxide adduct of a higher alcohol, an ethylene oxide adduct of a higher fatty acid, an ethylene oxide adduct of an alkyl phenol, an ethylene oxide adduct of an fatty acid amine, an ethylene oxide adduct of an fatty acid amide, an ethylene oxide adduct of a polyvalent alcohol, an ethylene oxide/propylene oxide block copolymer, and the like. The potyhydroxy type surfactants may include, for example, a glycerin monofatty acid ester, a pentaerythritol fatty acid ester, a sorbitan fatty acid ester, a sucrose fatty acid ester, an fatty acid amide of ethanol amine and an alkylene oxide adduct thereof, and the like. Among these polyhydroxy type surfactants, there may be advantageously employed a polyoxy ethylene sorbitan fatty acid ester, a polyoxy ethylene glyceryl monofatty acid ester, a polyoxy propylene monofatty acid ester, the sorbitan fatty acid ester, a polyoxy ethylene alcohol ether, and the like. These surfactants may be employed solely or in admixture with the other surfactant or surfactants.

The amount and the rate of the surfactant is not restricted to a particular one and may vary depending upon the desired properties of the topical preparation, although the surfactant may be generally contained in the range of from approximately 5% to 50% by weight, preferably from approximately 20% to 45% by weight, with respect to the total weight of the topical preparation in the case of the topical preparation being of a nonemulsion type and from approximately 1% to 20% by weight, preferably from approximately 5% to 15% by weight, with respect to the total weight thereof in the case of the topical preparation being of an emulsion type.

The topical preparation in accordance with the present invention may, as desired, contain an additive such as a filler, an aid for dissolving cyclosporin, a thickening agent, a colorant, a flavor, water, liquid paraffin, squalane, an emulsification stabilizer, a bactericide, a fungicide, and the like. The filler may be finely divided powder of an organic type or of an inorganic type. The particle size of the filler may range usually from approximately 0.1 μm to 20 μm, preferably from approximately 0.5 μm to 10 μm. Appropriate examples of the fillers may include silica, alumina, titania, resin powder, silicate powder, clay powder, sepiolite powder, mommorilonite powder, fluorinated mica powder, hydroxypropyl cellulose powder, and the like. The aid of dissolving cyclosporin may include, for example, an alkylene Glycol and a polyalkylene Glycol such as ethylene Glycol, propylene Glycol, isopropylene Glycol, polyethylene Glycol, polypropylene Glycol, and the like. The rate and the amount of the dissolving aid may range from approximately 0.2 part to 5 parts by weight with respect to part of the total weight of the organic solvent. The alkylene Glycol serves as accelerating the infusion or penetration of the cyclosporin through the skin.

The topical preparations according to the present invention may be applied in the form of an emulsion or a non-emulsion. When the topical preparations are formulated in a non-emulsion form, they may preferably comprise the following composition:

a. Cyclosporin: from approximately 0.1% to 10% by weight, preferably from approximately 1% to 7% by weight;

b. Organic solvent: from approximately 1% to 40% by weight, preferably from approximately 2% to 20% by weight;

c. Monovalent alcohol-fatty acid ester in liquid state at ambient temperature and/or the alkanol amine: from 1% to 15% by weight, preferably from approximately 3% to 10% by weight;

d. Oily substance in solid state at ambient temperature: from approximately 20% to 80% by weight, preferably from approximately 35% to 60% by weight;

e. Surfactant: from approximately 5% to 50% by weight, preferably from approximately 20% to 45% by weight; and f. Filler: from 0% to approximately 15% by weight, preferably from approximately 5% to 10% by weight.

When the lower alcohol is employed solely as the organic solvent for the topical preparation of the non-emulsion type, the lower alcohol may conveniently be contained at a rate ranging from approximately 2 to 15% by weight, preferably from approximately 3% to 10% by weight. In this case, the surfactant may conveniently be contained at a rate ranging from approximately 20% to 45% by weight, preferably from approximately 20% to 40% by weight and the oily substance may conventionally be contained at a rate in the range of from approximately 35% to 60% by weight, preferably from approximately 40% to 55% by weight. Further, the surfactant to be employed may have an HLB of 8 to 25, preferably from 9 to 12.

The topical preparation of the non-emulsion type may be formulated by mixing a cyclosporin solution in the organic solvent and the monovalent alcohol-fatty acid ester in liquid state at ambient temperature and/or the alkanol amine, mixing the resulting mixture with the oily substance and the surfactant, and adding the filler to the resulting mixture as needed, and then homogenizing the mixture.

The topical preparations in accordance with the present invention in an emulsion form may preferably comprise the composition as follows:

a. Cyclosporin: from approximately 0.1% to 10% by weight, preferably from approximately 1% to 7% by weight;

b. Organic solvent: from approximately 1% to 20% by weight, preferably from approximately 2% to 12% by weight;

c. Monovalent alcohol-fatty acid ester in liquid state at ambient temperature and/or the alkanol amine: from 1% to 15% by weight, preferably from approximately 3% to 10% by weight;

d. Oily substance in solid state at ambient temperature: from approximately 10% to 35% by weight, preferably from approximately 15% to.30% by weight;

e. Surfactant: from approximately 1% to 20% by weight, preferably from approximately 5% to 15% by weight;

f. Filler: from 0% to approximately 10% by weight, preferably from approximately 0.1% to 5% by weight; and g. Sterilized water: from approximately 30% to 75% by weight, preferably from approximately 40% to 50% by weight.

The topical preparations in the form of an emulsion may be prepared by mixing the components (a) to (f), inclusive, at elevated temperature to give an oily mixture in a liquid state, referred to hereinafter as "mixture A", and adding sterilized pure water, referred to hereinafter as "water B" to the mixture A with stirring at elevated temperature. The water B may be added at a rate of from approximately 30% to 75% by weight with respect to the total weight of the mixture A and the water B. To the water B may in advance be added an aid of infusion or penetration of cyclosporin through the skin, a viscosity adjusting agent, the bactericide, a water-soluble substance such as an alkanol amine. The infusion or penetration aid may include, for example, an alkylene glycol such as ethylene glycol, propylene glycol, butylene glycol, and the like. The viscosity adjusting agent may include, for example, a polyalkylene glycol such as polyethylene glycol, polypropylene glycol, and the like; a polyvalent alcohol such as glycerin and the like; and a water-soluble polymer such as carboxyvinyl polymer and the like. The topical preparations in the emulsion form may be of an oil/water type and of a water/oil type. For the topical preparations of the oil/water type, the surfactant having an HLB of 9 to 18 may preferably be employed; for the topical preparations of the water/oil type, the surfactant having an HLB of 2 to 8 may preferably be employed. To the topical preparations of the emulsion type may be added, as needed, a viscous oily substance such as liquid paraffin, glycerin, vaseline, and the like.

The topical preparations according to the present invention may be administered by applying them directly to the affected part of the skin or by applying them in the form of a patch, plaster, poultice, or the like to the affected part thereof, several times, e.g. once to thrice, per day. The number of applications may appropriately be increased or reduced depending upon the extent of the disease to be applied.

In accordance with the topical preparations of the present invention, a mixture of the cyclosporin solution in the organic solvent with the liquid monovalent alcohol-fatty acid ester and/or alkanol amine is contained in the oily substance in homogeneously dispersed manner. Hence, the topical preparations is so highly likely to infuse or penetrate through the skin that they can demonstrate highly therapeutic effects upon autoimmune or allergic skin diseases merely by applying them to the affected part of the skin. Further, the topical preparations are little irritative or extremely low in irritation to the skin so that they are highly safe.

The topical preparations according to the present invention are highly effective for the therapy of various dermal diseases such as atopic dermatitis, psoriasis, contact dermatitis, allergic contact dermatitis, alopecia, and the like. Further, they are effective for treating other dermal diseases, such as scald. The topical preparations can assist adapt a skin piece grafted to the site of skin grafting.

The present invention will be described more in detail by way of examples.

EXAMPLE 1

For a topical preparation, there were employed the components as follows:

Cyclosporin: 1% by weight

95% Ethanol: 3% by weight

Isopropyl myristate: 5% by weight

Olive oil: 48% by weight

Polyoxyethylene (5) glyceryl monostearate: 35% by weight

Finely divided silica (Aerosil 200) 8% by weight

The topical preparation was formulated by mixing isopropyl myristate, polyoxyethylene (5) glyceryl monostearate and olive oil with stirring at 50° C. to give a homogenous solution to which a solution of cyclosporin in ethanol was added, and the resulting mixture heated to 30°–35° C. was mixed with aerosil to give an ointment.

EXAMPLE 2

A topical preparation was prepared in substantially the same manner as in Example 1 using the components as follows:

Cyclosporin: 1% by weight

95% Ethanol: 5% by weight

Isopropyl myristate: 5% by weight

Olive oil: 47% by weight

Polyoxyethylene (5) glyceryl monostearate: 35% by weight

Finely divided silica (Aerosil 200) 7% by weight

EXAMPLE 3

A topical preparation was prepared in substantially the same manner as in Example 1 using the components as follows:

Cyclosporin: 2% by weight

95% Ethanol: 10% by weight

Isopropyl myristate: 5% by weight

Camellia oil: 44% by weight

Polyoxyethylene (5) glyceryl monostearate: 32% by weight

Finely divided silica (Aerosil 200) 7% by weight

EXAMPLE 4

After the skins of guinea pigs were sensitized with dinitrofluorobenzene (DNFB), DNFB were applied again, thereby causing the strong allergic reaction to emerge on the skins of the guinea pigs.

The efficacy of the topical preparations according to the present invention was observed with this experimental model.

Cyclophosphamide was intraperitoneally administered at the rate of 200 mg per kg three days before the sensitization of male Hartley guinea pigs, weighing from 40 grams to 500 grams, and 50 µl of a 10% DNFB solution in a 1:1 mixture of acetone and olive oil) was applied to one earlobe of each of the guinea pigs. At day 8, a dose of 20 µl of 0.5% or 0.1% DNFB solution in a 4:1 mixture of acetone and olive oil was applied to the both sides of the depilated abdominal portions of the guinea pigs, whereby contact dermal allergic reaction was induced.

After DNFB was then applied as an antigen to the corresponding sites of the both abdominal portions, the topical preparations prepared in Example 1 (containing cyclosporin at the rate of 0.1%, 1% and 10%) were applied in the amount of 50 μl thereto. This application was repeated twice a day at an interval of 8 hours. The first application of each topical preparation was conducted immediately after DNFB had been air dried.

The allergic reaction was evaluated at 24 hours, 48 hours and 72 hours after the application of the antigen in accordance with the following criteria: Rating 4=swell in red; rating 3=colored in red; rating 2=colored in pink; rating 1=a spot colored in pink; and rating 0=no change. The values as shown in Table 1 below represent the mean value plus or minus the standard error (SE).

The statistical treatment was conducted with Student's t-test, and a significant difference was justified if the error rate was $p<0.05$.

The application of the 0.5% DNFB solution caused the strongest allergic reaction over the time range from 24 hours to 48 hours after the application. The 0.1% cyclosporin ointment suppressed the allergic reaction to a considerable extent with no significant difference. On the other hand, the ointment containing 1% cyclosporin reduced the allergic reaction to a remarkable extent at 24 hours with the significant difference of $p<0.01$. Even at 48 hours and 72 hours, the allergic reaction was suppressed with the significant difference. Further, the ointment containing 10% cyclosporin demonstrated the significant suppression of the allergic, like the 1% cyclosporin ointment. As a control, the ointment base only did not suppress the allergic reaction at all. The results are shown in Table 1 below.

TABLE 1

| Test Samples | | | | |
| --- | --- | --- | --- | --- |
| Cyclosporin (%) | No. of guinea pigs | 24 hours | 48 hours | 72 hours |
| 0 | 9 | 3.4 ± 0.2 | 3.4 ± 0.2 | 2.7 ± 0.2 |
| 0.1 | 9 | 2.4 ± 0.3 | 2.7 ± 0.3 | 1.8 ± 0.3 |
| 1.0 | 9 | 0.7 ± 0.3** | 1.0 ± 0.3** | 1.0 ± 0.3** |
| 0 | 4 | 3.3 ± 0.3 | 3.3 ± 0.3 | 3.3 ± 0.3 |
| 10 | 4 | 0.8 ± 0.5* | 1.0 ± 0.6* | 1.0 ± 0.5 |

*$p < 0.05$
**$p < 0.01$

When the 0.1% DNFB solution was applied, the strongest allergic reaction was caused to appear at 48 hours after the application. The 0.1% cyclosporin topical preparation suppressed the allergic reaction to a remarkable extent with the significant difference of $p<0.01$. The allergic reaction was likewise suppressed even at 48 hours and 72 hours. On the other hand, the topical preparations containing 1% and 10% cyclosporin showed the reduction in the allergic reaction with the significant difference, like the topical preparation containing 0.1% cyclosporin. As a control, the ointment base only did not suppress the allergic reaction at all. The results are shown in Table 2 below.

TABLE 2

| Test Samples | | | | |
| --- | --- | --- | --- | --- |
| Cyclosporin (%) | No. of guinea pigs | 24 hours | 48 hours | 72 hours |
| 0 | 8 | 2.1 ± 0.3 | 3.1 ± 0.2 | 2.5 ± 0.2 |
| 0.1 | 8 | 0.3 ± 0.2** | 1.0 ± 0.2** | 0.8 ± 0.2** |
| 1.0 | 8 | 0.1 ± 0.1** | 0.4 ± 0.3** | 0.1 ± 0.1** |
| 0 | 4 | 2.0 ± 0.4 | 3.0 ± 0 | 2.3 ± 0.3 |
| 10 | 4 | 0 ± 0* | 0.5 ± 0.3* | 0.3 ± 0.3* |

*$p < 0.05$
**$p < 0.01$

EXAMPLE 5

Case 1:
A male patient, 27 years old, has been affected with atopic dermatitis since his age of 22 although a temporary remission had been gained at his age of 8 years from the atopic dermatitis since his age of 3. Various steroidal ointments were applied so far; they were found hardly effective. With the 10% cyclosporin ointment according to the present invention, an itch on his skin disappeared four to five hours after the application of the ointment and the lichenized erythra peculiar in the atopic dermatitis disappeared completely at day 3 after its application when the ointment was applied twice per day.

Case 2:
A male child, 6 years old, has been affected with atopic dermatitis since his age of 3 and was administered with Azeptin, Zaditen, and Rizaben as well as ointments such as Rinderon V, Locorten and Methaderm; however, no effect was recognized. The application of a 5% cyclosporin ointment according to the present invention eliminated an itch to his skin within 5 hours after the topical administration and the itch, erythema and wet erosion of the affected part had disappeared within 24 hours after the application thereof.

Case 3:
A male patient, 52 years old, was affected with psoriatic arthritis, and the 1% cyclosporin ointment according to the present invention was applied to the wet erythema with a clear borderline and the scales on the surface thereof. The 1% cyclosporin ointment improved the Auspitz phenomenon within 24 hours after the application with the erythema disappearing at day 3 from the application of the ointment.

EXAMPLE 6

In order to demonstrate the efficacy of the topical preparations according to the present invention, the ointments were prepared from the components as shown in Table 3 below and the efficacy thereof was evaluated in substantially the same manner as in Example 4. The evaluation results are shown in Table 3 below.

TABLE 3

| | Contents (% by weight) Experiment Nos. | | | | | | |
| --- | --- | --- | --- | --- | --- | --- | --- |
| Components | 1* | 2* | 3 | 4 | 5 | 6 | 7 |
| Cyclosporin | 5 | 5 | 5 | 5 | 10 | 5 | 10 |
| 95% Ethanol | 0 | 0 | 2 | 5 | 10 | 5 | 10 |
| Isopropyl myristate | 5 | 5 | 5 | 5 | 5 | 0 | 3 |
| Olive oil | 48 | 48 | 48 | 45 | 35 | 36 | 36 |
| Polyoxyethylene | 35 | 35 | 35 | 35 | 35 | 36 | 36 |

TABLE 3-continued

| Components | Contents (% by weight) Experiment Nos. | | | | | | |
|---|---|---|---|---|---|---|---|
| | 1* | 2* | 3 | 4 | 5 | 6 | 7 |
| glycol mono-stearate | | | | | | | |
| Aerosil | 5 | 7 | 5 | 5 | 5 | 6 | 6 |
| Triethanol amine | 2 | 0 | 0 | 0 | 0 | 3 | 2 |
| Efficacy | None | None | Yes | Yes | Yes | Yes | Yes |

*Comparative Examples

Comparative Examples

The following topical preparations containing cyclosporin were prepared for comparative purposes in conventional manner:

i. A caster oil suspension containing 5% by weight of cyclosporin;
ii. A suspension of 5% by weight of cyclosporin in castor oil containing 20% by weight of propylene glycol; and
iii. An ointment containing 10% by weight of cyclosporin, 43% by weight of olive oil, 10% by weight of ethanol, 7% by weight of polyoxyethylene (5) oleate, and by weight of silicon dioxide in colloidal state.

The topical preparations prepared in the manner as described hereinabove were evaluated for their pharmaceutical efficacy in substantially the same manner as in Example 4; however, none of them were found significantly effective.

EXAMPLE 7

For a topical preparation, there were employed the components as follows:

Cyclosporin: 5% by weight
95% Ethanol: 2% by weight
Isopropyl myristate: 7% by weight
Camellia oil: 40% by weight
Polyoxyethylene (5) glyceryl monostearate: 41% by weight
Finely divided silica (Aerosil 200) 5% by weight The topical preparation was formulated in substantially the same manner as in Example 1.

EXAMPLE 8

A topical preparation was prepared in substantially the same manner as in Example 1 using the components as follows:

Cyclosporin: 5% by weight
95% Ethanol: 5% by weight
Isopropyl myristate: 5% by weight
Camellia oil: 39% by weight
Polyoxyethylene (5) glyceryl monostearate: 39% by weight
Finely divided silica (Aerosil 200) 5% by weight

EXAMPLE 9

After each of the topical preparations prepared in Examples 7 and 8 were stored in a closed state for 6 months at relative temperature of 75% and temperature of 40° C., the content of cyclosporin within the topical preparation was measured. As a result, it was found that no substantial changes were observed between before and after storage. Thus, it is confirmed that cyclosporin is sustained in a stable state for a long period of time.

EXAMPLE 10

A mixture (A) was prepared by dissolving 50 grams of cyclosporin, 70 grams of 2-octyl dodecanol, 30 grams of isopropyl myristate, 20 grams of isotridecyl myristate, 10 grams of polyoxyethylene sorbitan monooleate (20), 50 grams of polyoxyethylene glyceryl monostearate (5), 10 grams of sorbitan monostearate, 30 grams of cetanol, 40 grams of sebacate and 30 grams of olive oil at 80 C. On the other hand, a mixture (B) was prepared by adding 30 grams of propylene glycol, 20 grams of diisopropanol amine, 2 grams of carboxyvinyl polymer, 1 gram of methyl p-hydroxybenoate, and 1 gram of propyl p-hydroxybenzoate to 596 ml of sterilized water and heating the mixture to approximately 82° C. As the two mixtures reached the predetermined temperatures, the mixture A was gradually added with vigorous stirring to the mixture B, thereby producing an emulsion. After the addition was completed, the heating was ceased and the temperature of the emulsion was stirred and cooled down to 60°–55° Then, sterilized water was added to make the total volume of the mixture 1 kg. The whole mixture was allowed to stand and defoamed, followed by filling in a vessel.

In the above composition, polyoxyethylenel glyceryl monostearate (5) can be replaced by 2.0% by weight of polyoxyethylene (2) cetyl ether; sorbitan monostearate can be replaced by squalane SK; and cetanol can be replaced by behenyl alcohol. Further, the total volume of the sterilized water used for the mixture (B) can be replaced by liquid paraffin.

EXAMPLE 11

A mixture (A) was prepared by dissolving 50 grams of cyclosporin, 50 grams of ethanol, 50 grams of isopropyl myristate, 50 grams of polyethylene glycol (400), 30 grams of dithyl sebacate, 80 grams of olive oil, 30 grams of polyoxyethylene monostearate (5), 30 grams of polyethylene glycol monostearate (40), and 20 grams of sorbitan monostearate at elevated temperature. On the other hand, a mixture (B) was prepared by dissolving 50 grams of polythylene glycol, 20 grams of diisopropanol amine, 10 grams of carboxyvinyl polymer, 1 gram of methyl p-hydroxybenoate, and 1 gram of propyl p-hydroxybenzoate in 528 ml of sterilized water at elevated temperature. The mixture A was gradually added with vigorous stirring to the mixture B, thereby producing an emulsion. After the addition was completed, the total volume of the mixture was increased to make 1 kg by adding sterilized water to the mixture.

In the above composition, ethanol can be replaced by behenyl alcohol, and diisopropanol amine can be replaced by triethanolamine.

EXAMPLE 12

A mixture (A) was prepared by dissolving 50 grams of cyclosporin, 10 grams of octyl alcohol, 50 grams of olive oil, 30 grams of isopropyl myristate, 25 grams of isotridecyl myristate, 20 grams of polyoxyethylene sorbitan monooleate (20), 60 grams of polyoxyethylenel glyceryl monostearate (5), 20 grams of sorbitan stearate, 30 grams of cetanol, 25 grams of stearic acid, and 35 grams of diethyl sebacate at 80° C.. On the other hand, a mixture (B) was prepared by adding and dissolving 20 grams of polythylene glycol, 20 grams of diisopropanol amine, 2 grams of carboxyvinyl polymer, 0.5 gram of methyl p-hydroxybenoate, and 0.5 gram of propyl p-hdroxybenzoate to and in approximately 400 ml of sterilized water by heating the mixture to 82° C. or higher. The mixture B was gradually added with vigorous stirring to the mixture A, thereby producing an emulsion. After the addition was completed, the heating was ceased and sterilized water was added at 80° C. to the resulting mixture with stirring at room temperature, thereby increasing the total volume of the mixture to make 1 kg. The whole mixture was allowed to stand and defoamed; then the ointment in cream form was filled in a container.

In the above composition, isopropyl myristate can be replaced by isopropyl palmirate.

EXAMPLE 13

A mixture (A) was prepared by dissolving 50 grams of cyclosporin, 30 grams of bees wax, 80 grams of 2,6-dimethyl-4-heptanol, 30 grams of olive oil, 40 grams of isotridecyl myristate, 20 grams of polyoxyethylene solbitol hexastearate (20), 60 grams of polyoxyethylenel glyceryl monostearate (5), 20 grams of polyoxyethylene (60) hardened castor oil, 40 grams of cetostearyl alcohol, and 40 grams of diethyl sebacate at 80° C. On the other hand, a mixture (B) was prepared by adding and dissolving 30 grams of polyethylene glycol, 20 grams of diisopropanol amine, 2 grams of carboxyvinyl polymer, 0.5 gram of methyl p-hydroxybenoate, and 0.5 gram of propyl p-hydroxybenzoate to and in 510 ml of sterilized water by heating the mixture to 82° C. or higher. The mixture (B) was gradually added with vigorous stirring to the mixture (A) maintained at 80° C. After the addition was completed, the heating was ceased and the mixture was cooled down to 60°–55° C. with stirring. Then, sterilized water heated to 80° C. was added to the resulting mixture with stirring at room temperature, thereby increasing the total volume of the mixture to make 1 kg. The whole mixture was allowed to stand and defoamed; then the resulting mixture was filled in a container.

In the above composition, the bees wax can be replaced by polyoxyethylene lanolyl alcohol or a bees wax derivative; isotridecyl myristate can be replaced by 0.2% by weight of silicone oil; polyoxyethylenel sorbitan oleate (20) can be replaced by polyoxyethylenel sorbitan-fatty acid ester; sorbitan monostearate can be replaced by squalane SK; and sterilized water can be replaced by liquid paraffin.

EXAMPLE 14

A mixture (A) was prepared by mixing 50 grams of cyclosporin, 80 grams of propylene glycol monocaprylate, 30 grams of isopropyl myristate, 30 grams of PEG monostearate (25E0), 30 grams of polyethylene glycol, 20 grams of isotridecyl myristate, 20 grams of cetanol, 50 grams of olive oil, 80 grams of whale wax, 30 grams of sorbitan monostearate, 30 grams of polyoxyethylene glyceryl monostearate (5), 30 grams of stearic acid, 20 grams of diisopropanol amine, and 40 grams of diethyl sebacate and heating the resulting mixture at 80° C. On the other hand, a mixture (B) was prepared by adding 30 grams of propylene glycol, 15 grams of diisopropanol amine, 2 grams of carboxyvinyl polymer, 0.5 gram of methyl p-hydroxybenoate, and 0.5 gram of propyl p-hydroxybenzoate to approximately 400 ml of sterilized water and heating the resulting mixture to 82° C. or higher. The mixture (B) was gradually added with vigorous stirring to the mixture (A) maintained at 80° C. or higher. After the addition was completed, the heating was ceased and the mixture was stirred to cool the temperature of the mixture to 60°–55° C., followed by adding sterilized water heated at 80° C. to the resulting mixture to increase the total volume of the mixture to make 1 kg. The whole mixture was allowed to stand and defoamed; then the resulting mixture was filled in a container.

EXAMPLE 15

A mixture (A) was prepared by mixing 50 grams of cyclosporin, 70 grams of 2-octyl dodecanol, 30 grams of isoprene glycol, 40 grams of diethyl sebacate, 30 grams of isopropyl myristate, 30 grams of isotridecyl myristate, 60 grams of whale wax, 30 grams of cetanol, 40 grams of stearic acid, 20 grams of POE (5) glyceryl monostearate, 20 grams of PEG monostearate (40EO), 10 grams of sorbitan monostearate, 50 grams of olive oil, and 1 gram of propylparaben and heating the mixture to 80° C.. On the other hand, a mixture (B) was prepared by adding 30 grams of butylene glycol, 20 grams of diisopropanol amine, and 1 gram of methylparaben to 460 ml of sterilized water and heating the resulting mixture to 82° C. or higher. The mixture (B) was gradually added with vigorous stirring to the mixture (A) maintained at 80° C. or higher. After the addition was completed, the heating was ceased and the temperature of the mixture was cooled down to 60°–55° C. with stirring. Then, sterilized water headed at 80° C. was added to the resulting mixture, thereby increasing the total volume of the mixture to make 1 kg. The whole mixture was allowed to stand and defoamed; then the resulting mixture was filled in a container.

EXAMPLE 16

A solution of 50 grams of cyclosporin in 80 grams of 2-octyl dodecanol was added to a warmed mixture of 40 grams of isopropyl myristate, 370 grams of olive oil, 378 grams of polyoxyethylene (5) glyceryl monostearate, 2 grams of polyoxyethylene (9) lauryl ether, and 10 grams of sorbitan monostearate, and 70 grams of aerosil was added to the resulting mixture, thereby yielding a topical preparation of a non-emulsion type.

EXAMPLE 17

The efficacy of the creamy ointment containing cyclosporin, prepared in substantially the same manner as in Example 15, was confirmed by applying it to the transplant of the skin sections of mice.

The skin sections of 10 male CBA mice of 5 weeks were transplanted to male C3H/HeN mice of the same week. To the transplanted sites and the portions surrounding them was applied approximately 0.1 gram of the ointment prepared in Example 12 two times per day until the transplanted sections eventually fell off. The results are shown in Table 4 below.

TABLE 4

| Cyclosporin (%) | Period of Transplantation* | Effect of Extension | Significant Difference** |
|---|---|---|---|
| 5.0 | >60 | >397 | $p < 0.001$ |
| 1.0 | 31.3 ± 1.43 | 207 | $p < 0.001$ |
| 0.0 (as control) | 15.1 ± 0.78 | 100 | — |

*mean value ± SE
**Student's t-test

For a control group in which a cream without cyclosporin was applied, the transplanted skin specimens fell off for an average period of transplantation of 12.7 days, while a group in which a cream containing 5% cyclosporin was applied had all the transplanted skin sections grow for 60 days or longer. For a group in which a cream containing 1% cyclosporin was applied, the period of transplantation for which the transplanted skin sections grew was extended with significant difference to mean 31.3 days.

EXAMPLE 18

Eight Hartley male guinea pigs weighing approximately 300 grams were intraperitoneally administered with 150 mg/kg of cyclophosphamide, and 50 μl of a 10% dinitroflurobenzene (DNFB) solution was applied to one earlobe of each guinea pig in three days after the intraperitoneal administration. The DNFB solution was prepared by dissolving the predetermined amount of the DNFB in a 1:1 mixture of acetone with olive oil. After 8 days, the hairs on the both abdominal parts were cut off and 20 μl of a 0.1% DNFB solution was applied to the depilated abdominal parts of the guinea pigs to induce contact dermal allergy. Immediately thereafter, the cyclosporin ointment prepared in substantially the same manner as in Example 15 was applied to the parts to which the DNFB solution was applied, followed by applying the cyclosporin ointment thereto in 8 hours. To a control group, the base used in Example 15 without cyclosporin was applied in accordance with the same schedule as described hereinabove.

The allergic reaction was determined in 24 hours, 48 hours and 72 hours after the application of the DNFB solution as the antigen, and the rating was: 4=swell in red; 3=colored in red; 2=inflammation causing the skin to turn pink; 1=inflammation causing the skin to turn pale pink; and 0=no change. The results are shown in Table 5 below.

TABLE 5

| Cyclosporin | Severity of Dermal Reaction (mean value ± SE) | | |
|---|---|---|---|
| (%) | 24 hours | 48 hours | 72 hours |
| 1.0 | 0.0 ± 0.0** | 0.3 ± 0.2** | 0.1 ± 0.1** |
| 0.1 | 0.3 ± 0.3** | 0.9 ± 0.2** | 0.7 ± 0.3** |
| 0.0 (control) | 2.2 ± 0.3** | 3.1 ± 0.2** | 2.4 ± 0.2** |

**$p < 0.001$ in Student's t-test

In these experiments, the strongest allergic reaction was induced over the range extending from 24 hours to 48 hours after the application of the DNFB solution. The ointment containing 1.0% cyclosporin strongly suppressed the allergic reaction and the ointment containing 0.1% cyclosporin suppressed the allergic reaction with significant difference.

What is claimed is:

1. A topical preparation comprising: (a) approximately 0.1 to 10% by weight cyclosporin; (b) an organic solvent in which said cyclosporin is dissolved; and (c) approximately 1% to 15% by weight of a skin penetration enhancer, said skin penetration enhancer being at least one member selected from the group consisting of alkanolamines and monovalent alcohol esters of myristic acid, adipic acid and sebacic acid, said (c) being liquid at 25° C.

2. A topical preparation as claimed in claim 1, wherein said organic solvent is aliphatic alcohol which is liquid at 25° C., 3. A topical preparation as claimed in claim 2, wherein said aliphatic alcohol is a lower alcohol.

4. A topical preparation as claimed in claim 3, wherein said lower alcohol is ethanol.

5. A topical preparation as claimed in claim 2, wherein said aliphatic alcohol is a higher alcohol having a branched chain and at least 8 carbon atoms.

6. A topical preparation as claimed in claim 5, wherein said higher alcohol is 2-octyldodecanol.

7. A topical preparation as claimed in claim 1, wherein said organic solvent is a monoester of a fatty acid with a polyhydric alcohol 8. A topical preparation as claimed in claim 7, wherein said monoester is propyleneglycol monocaprate or propylene glycol monocaprylate.

9. A topical preparation as claimed in claim 1, wherein said organic solvent is present amount ranging from approximately 0.5 part to 10 parts by weight per part by weight of said cyclosporin.

10. A topical preparation as claimed in claim 1 wherein said preparation is an emulsion.

11. A topical preparation as claimed in any one of claims 1,2,3,4,5,6,7,8 or 9 further comprising a vegetable oil.

12. topical preparation as claimed in any one of claims 1,2,3,4,5,6,7,8, or 9 further comprising a surfactant.

13. A topical preparation as claimed in any one of claims 1,2,3,4,5,6,7,8 or 9 further comprising a filler.

14. A topical preparation as claimed in any one of claims 1,2,3,4,5,6,7,8, or 9 further comprising at least one of an alkylene glycol and a polyalkylene glycol said preparation is an emulsion.

15. A topical preparation comprising: (a) approximately 0.1% to 10% by weight of cycliosporin; (b) approximately 2% to 15% by weight of lower alcohol; and (c) approximately 1% to 15% by weight of a skin penetration enhancer, said skin penetration enhancer being at least one member selected from the group consisting of alkanolamines and monovalent alcohol esters of myristic acid, adipic acid and sebacic acid.

16. A topical preparation as claimed in claim 15, wherein said lower alcohol is at least one member selected from the group consisting of ethanol, isopropanol, propanol and isobutanol.

17. A topical preparation as claimed in claim 15 wherein said preparation is an emulsion.

18. A topical preparation as claimed in claim 15, further comprising from approximately 5% to 10% by weight of a filler.

19. A topical preparation comprising 0.1% to 10% by weight of cyclosporin; 2% to 15% by of ethanol; 1% to 15% by weight of isopropyl myristate; 35% to 60% by weight of olive or camellia oil; 20% to 40% by weight of a surfactant; and 5% to 10% by weight of silica.

* * * * *

UNITED STATES PATENT AND TRADEMARK OFFICE
CERTIFICATE OF CORRECTION

PATENT NO.  : 5,504,068

DATED       : April 2, 1996

INVENTOR(S) : Komiya et al

It is certified that error appears in the above-identified patent and that said Letters Patent is hereby corrected as shown below:

Col. 18, line 20, after "present" insert --in an--
       line 27, before "topical" insert --A--
       line 33, delete "said preparation is"
       line 34, delete "an emulsion"
       line 55, after "olive" insert --oil--

Signed and Sealed this

Twenty-fifth Day of February, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,504,068

DATED : April 2, 1996

INVENTOR(S) : Komiya et al.

It is certified that error appears in the above-identified patent and that said Letters Patent is hereby corrected as shown below:

Columns 1 thru 18 of the printed patent should be deleted, and substituted with the attached columns 1 thru 18.

Signed and Sealed this

Seventeenth Day of June, 1997

Attest:

BRUCE LEHMAN

Attesting Officer

Commissioner of Patents and Trademarks

TOPICAL PREPARATIONS CONTAINING CYCLOSPORIN

TECHNICAL FIELD

The present invention relates to topical preparations containing cyclosporin as a major active component. The topical preparations containing cyclosporin include topical preparations in the form of emulsions and non-emulsions.

The term "cyclosporin" as used in this application is intended to mean a single substance or a mixture of a group of cyclosporin antibiotics which are described in detail in Japanese Patent Laid-open Publication (kokai) No. 2-17,127.

BACKGROUND ART

Cyclosporin is known as an immune inhibitor and it has extensively been employed in the field of the transplant of organs including the kidney. Recently, cyclosporin has become recognized as being effective in the treatment of various diseases that are caused mainly from autoimmune reaction. A number of literature articles have already been published which report the efficacy of cyclosporin for arthritis. Autoimmune diseases to which cyclosporin has been applied or proposed to be applied include, for example, autoimmune blood diseases, chronic bronchial asthma, systemic erythematosus, polymyositis, systemic scleroderma, Wegner syndrome, myasthenia gravis, psoriasis vulgaris, autoimmune intestinal diseases (idiopathic ulcerative colitis, Crohn disease), sarcoidosis, multiple sclerosis, juvenile diabetes mellitus, uveitis, psoriatic rheumatoid, glomerulonephritis, and the like.

As described hereinabove, cyclosporin contributes to the inhibition of rejection at the time of transplanting organs and autoimmune therapy; however, it is also known that it may often cause a severely adverse affect upon the kidney when administered orally over a long period of time and this toxicity to the kidney has prevented cyclosporin from being extensively employed. It can be noted that there are morbid states of the skin, eye or joint to which topical preparations can be applied. In the case of diseases that can be treated with topical preparations, it is advantageous to avoid systemic administration that might cause disturbances to the kidney. If the focus of a disease is restricted to a layer of the dermis, topical administration through the epidermis is more advantageous than other modes of administration because it can reduce the amount of a medicine to be administered and, further, the efficacy of the medicine can be enhanced by a localized concentration of the medicine, while systemic side effects can be reduced. Topical preparations are among the most effective drug delivery systems (DDS) for cyclosporin.

On the other hand, it is extremely difficult to formulate cyclosporin into topical preparations so as to maintain its highly therapeutical effect, unlike water-soluble or low-molecular weight, pharmaceutically effective substances. One of the reasons for this difficulty is because the cyclosporin is a large cyclopolypeptide having a molecular weight of greater than 1,200 which makes it difficult for the cyclosporin to infuse or penetrate through the horny skin layer into the target site present in the dermis layer. Another reason for the difficulty is that cyclosporin is insoluble in water and the number of organic solvents in which the cyclosporin can be dissolved is limited. As such specific organic solvents, a lower alkanol such as ethanol or isopropanol may be generally employed. However, such a lower alkanol is too highly irritative to the skin when it is employed for topical preparations in a relatively high concentration, to provide a safe topical preparation. On the other hand, when the lower alcohol is employed in a relatively low concentration for topical preparations, the ability of the cyclosporin to be dispersed uniformly in the topical preparations may be impaired, thereby reducing the therapeutical effect.

Reports on clinical research with cyclosporin ointments have been published to the effect that a 10% cyclosporin formulation may be pharmaceutically effective or ineffective, so that its pharmaceutical effects may or may not be reproduced. Some reports describe specific cyclosporin formulations without describing any clear pharmaceutical effects.

For example, Japanese Patent Laid-open Publication No. 2-17,127 discloses compositions which contain, as essential components, cyclosporin and a mono- or poly-unsaturated fatty acid or an unsaturated alcohol, each having from 12 to 24 carbon atoms. The mono- and poly-unsaturated fatty acids may include, for example, vaccenic acid, linoleic acid, linolenic acid, elaidic acid, erucic acid, and the like. The unsaturated alcohols may include, for example, vaccenyl alcohol, linoleyl alcohol, linolenyl alcohol, elaidyl alcohol, erucyl alcohol, and the like. Further, it teaches that the compositions are effective against various skin diseases; however, that publication does not specify its pharmaceutical effects and refers merely to the ability of the cyclosporin to infuse or penetrate through the skin and to the concentration of the cyclosporin. The publication is thoroughly silent about the extent, for example, to which the cyclosporin is effective against psoriatic diseases.

Much of the literature states that cyclosporin is effective against skin diseases. For example, atopic dermatitis is discussed in Acta. Derm. Venerol.: Suppl. 144, 136-138 (1989) and it is reported that an alcoholic oily gel containing cyclosporin in the concentration of 10% by weight is effective against atopic dermatitis. Further, Arch. Derm.: 125, p. 570 (1989) reports that an alcoholic oily gel of 10% (by weight) cyclosporin is effective.

Contact-type dermatitis is discussed, for example, in Arch. Dermato-1: 125, 568 (1989) which reports that cyclosporin was employed in a human DNCB test with no effect. Further, Contact Dermatitis: 19, 129-132 (1988) reviews three formulations: a 10% cyclosporin formulation in Labrafil (polyoxyl-5-oleate, olive oil and ethanol), a 5% cyclosporin formulation in castor oil, and a 5% cyclosporin formulation in castor oil containing 20% propylene glycol; however, it states that the effects of these formulations are not satisfactory and that a more effective solvent is required. In addition, Contact Dermatitis, 20, 155-156 states that none of three formulations, or 0.1%, 1% and 10% cyclosporin formulations, are effective at all against contact dermatitis.

The pharmaceutical effect of cyclosporin upon psoriasis is described, for example, in Clin. Res., 34, 1007A (1986), which reports that topical administration of cyclosporin is not effective for the therapy of psoriasis, although neither the concentration of cyclosporin nor the composition thereof are specified. It is also reported in Lancet, 1, 806 (1987) that a 2% by weight cyclosporin (on ointment base) is only as effective upon psoriasis as a placebo. Further, J. Amer. Acad. Dermatol., 18, 378–379 (1988) reports that the effect of a 5% cyclosporin solution in olive oil is equal to that of the sole use of olive oil employed as the base in the previous case. In addition, J. Amer. Acad. Dermatol., 22, 126–127 (1990) states that a gel comprising 10% cyclosporin, 43% olive oil, 10% ethanol, 30% polyoxyl-5-oleate and 7% colloidal silica did not produce any effect upon psoriasis. Furthermore, it is reported in Brit. J. Derm., 122, 113–114 (1990) that a 5% (by weight) cyclosporin ointment was not effective.

Reports for alopecia areata have been published, for example, in Lancet, 2, 803–804 (1986) where it is reported that a 2% cyclosporin oily solution was effective. In addition, Lancet, 2, 971–972 (1986) reports that a 5% (wc) cyclosporin formulation in oil was effective against alopecia areata. On the other hand, Acta. Derm. Venereol., 69, 252–253 (1989) reports that a 10% cyclosporin oily preparation was not effective. Furthermore, J. Amer. Acad. Dermatol., 22, 251–253 (1989) reports that a 5% cyclosporin formulation was effective against male alopecia, although no specific compositions are described therein.

Based on a review of the literature as described hereinabove, it is difficult to draw the conclusion that cyclosporin is topically effective against the skin diseases as specified hereinabove. Even if it could be said that cyclosporin would be effective against the above-mentioned skin diseases, it can be concluded that cyclosporin should be employed in a considerably large amount. If cyclosporin preparations are not topically effective against skin diseases or if the effect is not satisfactory, it can be concluded in many occasions that the formulation components and/or the dosage are inappropriate. In summary, no conventional topical cyclosporin preparations achieve the object of utilizing cyclosporin effectively.

DISCLOSURE OF INVENTION

The primary object of the present invention is to provide a topical preparation containing cyclosporin, which acts effectively upon skin diseases and is highly safe.

Another object of the present invention is to provide a topical preparation containing cyclosporin, which has a lower concentration of a lower alcohol.

A further object of the present invention is to provide a highly safe topical preparation containing cyclosporin, which does not contain any quantity of a lower alcohol.

One aspect of the present invention provides a topical preparation containing (a) cyclosporin; (b) an organic solvent in which the cyclosporin is dissolved; (c) an ester of a fatty acid with a monovalent alcohol, which is liquid at 25° C. and which has a total number of carbon atoms of 8 or more, and/or an alkanol amine which is liquid at 25° C.; (d) an oily substance which is a solid at 25° C.; and (e) a surfactant wherein the amount of the cyclosporin ranges from 0.1% by weight to 10% by weight and the total amount of the ester of the fatty acid with the monovalent alcohol and/or the alkanol amine ranges from 1% by weight to 15% by weight.

Another aspect of the present invention provides a topical preparation containing (a) cyclosporin; (b) a lower alcohol; (c) a fatty acid ester which is liquid at 25° C. and/or an alkanol amine which is liquid at 25° C.; (d) an oily substance which is solid at 25° C.; and (e) a surfactant, wherein the amount of the cyclosporin ranges from 0.1% by weight to 10% by weight and the total amount of the ester of the fatty acid with the monovalent alcohol and/or the alkanol amine ranges from 1% by weight to 15% by weight.

Another aspect of the present invention provides a topical preparation containing (a) cyclosporin; (b) a lower alcohol; (c) a fatty acid ester which is liquid at 25° C. and/or an alkanol amine which is liquid at 25° C.; (d) an oily substance which is solid at 25° C.; and (e) a surfactant, wherein the amount of the cyclosporin ranges from 0.1% by weight to 10% by weight, the amount of the lower alcohol ranges from 2% by weight to 15% by weight; and the total amount of the fatty acid ester and/or the alkanol amine ranges from 1% by weight to 15% by weight.

The cyclosporin-containing topical preparations according to the present invention differ from the conventional cyclosporin topical preparations as reported in the aforesaid literature in achieving the objects of the present invention by using a reduced amount of cyclosporin.

The topical preparations containing cyclosporin according to the present invention offer the following advantages:

1. They are superior in therapeutic effect;
2. They are highly stable (i.e., cyclosporin does not separate from the topical preparations, no crystallization of cyclosporin occurs, and there is no chemical reaction of cyclosporin with any other components of the compositions);
3. They are easily administered topically;
4. They contain cyclosporin in a highly uniformly dispersed state; and
5. They are highly safe.

In determining the formulations of the topical preparations according to the present invention, the selection of each component of the formulation and the concentrations of the components are significant factors. For example, when the topical preparations are employed in the form of an ointment, the pharmaceutical effect of the ointment, the biological activity of the ointment, and the physicochemical stability of the ointment should be taken into account. Heretofore, a higher saturated fatty acid or a fatty acid such as oleic acid or 12-hydroxystearic acid has been employed as an ointment base. Among those fatty acids, lauric acid, myristic acid, palmitic acid and stearic acid have been employed to form soap, together with an alkali, particularly potassium hydroxide, which in turn helps emulsify the formulated medicine.

It should be noted, however, that the fatty acid, whether it is employed as is or in the form of potassium soap as an ointment base, for cyclosporin-containing topical preparations according to the present invention, has little effect in emulsifying cyclosporin in the topical preparations, and the pharmaceutical effect and stability of the ointment may be impaired.

DESCRIPTION OF THE PREFERRED EMBODIMENTS

The topical preparations according to the present invention contain cyclosporin, as a major active component, in a concentration ranging from 0.1% to 10% by weight, preferably from 1% by weight to 7% by weight. It is noteworthy here that the topical preparations of the present invention can demonstrate highly therapeutic effects with such a low concentration of cyclosporin.

The topical preparations according to the present invention contain an organic solvent for cyclosporin which is liquid at ambient temperature (25° C.) and which can dissolve the cyclosporin. Such organic solvents include aliphatic alcohols and fatty acid esters of polyvalent alcohols.

As the aliphatic alcohols, there may be employed any lower alcohol or higher alcohol as long as it is liquid at ambient temperature. The alcohol may be straight or branched and may be saturated or unsaturated. Specific examples of such aliphatic alcohols include lower alcohols such as ethanol, propanol, isopropanol, butanol, and the like, and higher alcohols such as octyl alcohol, nonyl alcohol, decyl alcohol, 2-octyl dodecanol, 2,6-dimethyl-4-heptanol, oleyl alcohol, and the like. The branched higher alcohols are preferred as the organic solvent for the cyclosporin.

The polyvalent alcohol-fatty acid ester may be represented by the following formula:

$$R^1COOR^2OH$$

where $R^1$ is an alkyl group having from 4 to 12 carbon atoms, preferably from 6 to 10 carbon atoms; and $R^2$ is an alkylene group having from 2 to 4 carbon atoms.

Specific examples of the polyvalent alcohol fatty acid ester include, for example, propylene glycol caprylate, propylene glycol caprate, butylene glycol caprylate, butylene glycol caprate, glycol butyrate, and propylene glycol butyrate.

The organic solvents as described hereinabove may be employed singly or in admixture with other organic solvents. Mixtures advantageously contain the lower alcohol in the range from approximately 5% to 60% by weight, preferably from approximately 10% to 50% by weight.

The organic solvents may be admixed with the cyclosporin in an amount ranging from approximately 0.5 part to 10 parts by weight, preferably from approximately 1 part to 5 parts by weight, per part by weight of cyclosporin. As the organic solvent, a lower alcohol, particularly ethanol, is preferred. The lower alcohol can serve as a solvent for the cyclosporin as well as act to accelerate the action of the cyclosporin in infusing or penetrating through the skin.

The amount of the lower alcohol admixed with the cyclosporin is preferably 2% by weight or more with respect to the total weight of the topical preparation, in order to accelerate the rate of infusion or penetration of the cyclosporin through the skin. If the concentration of the lower alcohol is greater, the extent of irritation becomes so severe that the concentration of the lower alcohol must be reduced to 15% by weight or less with respect to the total weight of the topical preparation. It is to be noted, however, that the concentration of the lower alcohol preferably ranges from 3% to 6% by weight with respect to the total weight of the topical preparation, in order to maximize the ability of the cyclosporin for infusion or penetration through the skin and to provide a low degree of irritation.

For the topical preparations according to the present invention, it is preferred to use an organic solvent having a boiling point of 160° C. or higher, preferably 180° C. or higher and which is sparingly volatile or volatilizable. Such organic solvents include, for example, higher aliphatic alcohols having 8 carbon atoms or more and divalent alcohol-fatty acid esters.

The topical preparations according to the present invention contain the ester of the fatty acid in liquid state at ambient temperature in combination with the monovalent alcohol and/or the alkanol amine. The fatty acid ester of the monovalent alcohol may have 8 carbon atoms or more, preferably 12 carbon atoms or more.

The monovalent alcohol component of the monovalent alcohol-fatty acid esters may be a residue of a straight- or branch-chained aliphatic alcohol having from 1 to 22 carbon atoms, preferably from 2 to 18 carbon atoms. The fatty acid component may be a straight-chained or branch-chained, monovalent or divalent fatty acid having from 4 to 22 carbon atoms, preferably from 6 to 18 carbon atoms. The monovalent alcohol and fatty acid components may in each case contain an unsaturated bond. The monovalent alcohol component may be, for example, ethanol, propanol, isopropanol, butanol, hexanol, octanol, isooctanol, dodecanol, isododecanol, myristyl alcohol, cetyl alcohol, hexadecyl alcohol, 2-ethylhexyl alcohol, 2-octyl dodecanol and the like. The fatty acid component may be, for example, a monovalent fatty acid such as butyric acid, octanoic acid, nonanoic acid, caprylic acid, capric acid, myristic acid, palmitic acid, stearic acid, linoleic acid, linolic acid, and erucic acid, or a divalent fatty acid such as succinic acid, adipic acid, pimelic acid, suberic acid, azelaic acid, sebacic acid, and dodecane diacid. Preferred examples of the fatty acid esters with the monovalent alcohols include, for example, monovalent fatty acid esters such as ethyl myristate, isopropyl myristate, isotridecyl myristate, isopropyl laurate, isopropyl caprylate, isopropyl palmitate, isopropyl butyrate, amyl butyrate, and octyl butyrate, and a divalent fatty acid ester such as diethyl succinate, diisopropyl succinate, diethyl adipate, diisopropyl adipate, diisooctyl adipate, dioctyl adipate, didecyl adipate, decyl isooctyl adipate, diethyl azelate, diisopropyl azelate, diisooctyl azelate, diethyl sebacate, diisopropyl sebacate, dibutyl sebacate, and dioctyl sebacate.

Specific examples of the alkanol amines include, for example, diethanol amine, triethanol amine, isopropanol amine, triisopropanol amine, dibutanol amine, tributanol amine, and the like.

The monovalent alcohol-fatty acid ester and the alkanol amine can serve to improve the ability of the cyclosporin in the organic solvents to infuse or penetrate through the skin as well as serving the purpose of homogeneously dispersing the cyclosporin, dissolved in the organic solvents, in the oily substance in solid form. The concentrations of these compounds will usually range from approximately 1% to 15% by weight, preferably from approximately 3% to 10% by weight, with respect to the total weight of the topical preparation. Further, these compounds may be employed in an amount ranging from approximately 2 parts to 5 parts by weight, preferably from approximately 2.5 parts to 4 parts by weight, per part by weight of the organic solvent or solvents.

The topical preparations according to the present invention contain the oily substance in solid form at ambient temperature. It is noted that the term "solid" as used herein is intended to mean semisolid as well as solid. The oily substance may be, for example, an alcohol, a fatty acid, an ester, a triglyceride, wax, vaseline, or the like. The alcohol may be, for example, palmityl alcohol, stearyl alcohol, eicosyl alcohol, glycerine, polyglycerin, or the like. The fatty acid may be, for example, palmitic acid, stearic acid, oleic acid, arachic acid, behenic acid, montanic acid, melissic acid, sebacic acid, and the like. The ester may be, for example, butyl stearate, hexyl laurate, myristyl myristate, dodecyl oleate, 2-octyldodecyl myristate, hexyl decyl octanoate, cetyl lactate, glyceryl caprate, glyceryl caprilate, or the like. As the triglyceride, there may be employed a variety of materials originating from sources such as animals or naturally occurring plants or vegetables, which are generally called fats and oils and which are commercially available. Suitable fats and oils include, for example, a large variety of vegetable oils, cow fats, liver fats, lanolin, lard, and the like. Preferred are vegetable oils, particularly olive oil, camellia oil, soybean oil, rapeseed oil, corn oil, castor oil, safflower oil, and the like. There may also be employed fish oil rich in eicosapentadecanoic acid that has recently drawn increasing attention due to its action against allergy and malignant tumors.

The amount of the oily substance is not particularly restricted and may be any arbitrary amount in accordance with the desired properties of the topical preparations. Generally, the amount of the oily substance will range from approximately 1 part to 10 parts by weight, preferably from approximately 2 parts to 8 parts by weight, per part by weight of the total weight of the organic solvent and the monovalent alcohol-fatty acid ester and/or the alkanol amine, which is in liquid state at room temperature.

A surfactant is contained in the topical preparations according to the present invention and may be selected from a variety of surfactants, including anionic, cationic, non-ionic and amphoteric ones. The non-ionic surfactants are preferably selected in terms of a low degree of irritation to the skin. The non-ionic surfactants may be, for example, an ethylene oxide type surfactant, a polyhydroxy type surfactant, a polymer type surfactant, or the like. The ethylene oxide type surfactants may include, for example, an ethylene oxide adduct of a higher alcohol, an ethylene oxide adduct of a higher fatty acid, an ethylene oxide adduct of an alkyl phenol, an ethylene oxide adduct of a fatty acid amine, an ethylene oxide adduct of a fatty acid amide, an ethylene oxide adduct of a polyvalent alcohol, an ethylene oxide/propylene oxide block copolymer, and the like. The polyhydroxy type surfactants may include, for example, a glycerin monofatty acid ester, a pentaerythritol fatty acid ester, a sorbitan fatty acid ester, a sucrose fatty acid ester, a fatty acid amide of ethanol amine and an alkylene oxide adduct thereof, and the like. Among these polyhydroxy type surfactants, there may be advantageously employed a polyoxy ethylene sorbitan fatty acid ester, a polyoxy ethylene glyceryl monofatty acid ester, a polyoxy propylene monofatty acid ester, a sorbitan fatty acid ester, a polyoxy ethylene alcohol ether, and the like. These surfactants may be employed singly or in admixture another surfactant or surfactants.

The amount and the ratio of the surfactant is not particularly restricted and may vary depending upon the desired properties of the topical preparation, although the surfactant may be generally present in the range of from approximately 5% to 50% by weight, preferably from approximately 20% to 45% by weight, with respect to the total weight of the topical preparation in the case of the topical preparation being of a non-emulsion type and from approximately 1% to 20% by weight, preferably from approximately 5% to 15% by weight, with respect to the total weight thereof in the case of the topical preparation being of an emulsion type.

The topical preparation in accordance with the present invention may, if desired, contain an additive such as a filler, an aid for dissolving cyclosporin, a thickening agent, a colorant, a flavor, water, liquid paraffin, squalane, an emulsification stabilizer, a bactericide, a fungicide, and the like. The filler may be finely divided powder of an organic type or of an inorganic type. The particle size of the filler will usually range from approximately 0.1 $\mu$m to 20 $\mu$m, preferably from approximately 0.5 $\mu$m to 10 $\mu$m. Examples of appropriate fillers include silica, alumina, titania, resin powder, silicate powder, clay powder, sepiolite powder, montmorillonite powder, fluorinated mica powder, hydroxypropyl cellulose powder, and the like. Aids for dissolving cyclosporin include, for example, an alkylene glycol and polyalkylene glycols such as ethylene glycol, propylene glycol, isopropylene glycol, polyethylene glycol, polypropylene glycol, and the like. The amount of the dissolving aid may range from approximately 0.2 part to 5 parts by weight per part of the total weight of the organic solvent. The alkylene glycol serves to accelerate the infusion or penetration of the cyclosporin through the skin.

The topical preparations according to the present invention may be applied in the form of an emulsion or a non-emulsion. When the topical preparations are formulated in a non-emulsion form, they preferably comprise the following:

a. Cyclosporin: approximately 0.1% to 10% by weight, preferably approximately 1% to 7% by weight;

b. Organic solvent: approximately 1% to 40% by weight, preferably approximately 2% to 20% by weight;

c. Monovalent alcohol-fatty acid ester in liquid state at ambient temperature and/or the alkanol amine: 1% to 15% by weight, preferably approximately 3% to 10% by weight;

d. Oily substance in solid state at ambient temperature: approximately 20% to 80% by weight, preferably approximately 35% to 60% by weight;

e. Surfactant: approximately 5% to 50% by weight, preferably approximately 20% to 45% by weight; and f. Filler: 0% to approximately 15% by weight, preferably approximately 5% to 10% by weight.

When a lower alcohol is employed alone as the organic solvent for the topical preparation of the non-emulsion type, the lower alcohol may conveniently be present in a concentration of approximately 2 to 15% by weight, preferably approximately 3% to 10% by weight. In this case, the surfactant may conveniently be present in a concentration of approximately 20% to 45% by weight, preferably approximately 20% to 40% by weight and the oily substance may conveniently be present in a concentration of approximately 35% to 60% by weight, preferably approximately 40% to 55% by weight. Further, the surfactant to be employed may have an HLB of 8 to 25, preferably from 9 to 12.

The topical preparation of the non-emulsion type may be formulated by mixing a cyclosporin solution in the organic solvent and the monovalent alcohol-fatty acid ester in liquid state at ambient temperature and/or the alkanol amine, mixing the resulting mixture with the oily substance and the surfactant, and adding the filler to the resulting mixture as needed, and then homogenizing the mixture.

The topical preparations in accordance with the present invention in an emulsion form preferably comprise the following:

a. Cyclosporin: approximately 0.1% to 10% by weight, preferably approximately 1% to 7% by weight;
b. Organic solvent: approximately 1% to 20% by weight, preferably approximately 2% to 12% by weight;
c. Monovalent alcohol-fatty acid ester in liquid state at ambient temperature and/or the alkanol amine: 1% to 15% by weight, preferably approximately 3% to 10% by weight;
d. Oily substance in solid state at ambient temperature: approximately 10% to 35% by weight, preferably approximately 15% to 30% by weight;
e. Surfactant: approximately 1% to 20% by weight, preferably approximately 5% to 15% by weight;
f. Filler: 0% to approximately 10% by weight, preferably approximately 0.1% to 5% by weight; and
g. Sterilized water: approximately 30% to 75% by weight, preferably approximately 40% to 50% by weight.

The topical preparations in the form of an emulsion may be prepared by mixing the components (a) to (f), inclusive, at elevated temperature to give an oily mixture in a liquid state, referred to hereinafter as "mixture A", and adding sterilized pure water, referred to hereinafter as "water B" to the mixture A with stirring at elevated temperature. The water B may be added in the amount of approximately 30% to 75% by weight with respect to the total weight of the mixture A and the water B. To the water B may in advance be added an aid for infusion or penetration of cyclosporin through the skin, a viscosity adjusting agent, a bactericide, and/or a water-soluble substance such as an alkanol amine. The infusion or penetration aid may include, for example, an alkylene glycol such as ethylene glycol, propylene glycol, butylene glycol, and the like. The viscosity adjusting agent may be, for example, a polyalkylene glycol such as polyethylene glycol, polypropylene glycol, and the like; a polyvalent alcohol such as glycerin and the like; and a water-soluble polymer such as carboxyvinyl polymer and the like. The topical preparations in the emulsion form may be of an oil/water type or of a water/oil type. For the topical preparations of the oil/water type, a surfactant having an HLB of 9 to 18 is preferably employed; for the topical preparations of the water/oil type, a surfactant having an HLB of 2 to 8 is preferably employed. To the topical preparations of the emulsion type may be added, as needed, a viscous oily substance such as liquid paraffin, glycerin, vaseline or the like.

The topical preparations according to the present invention may be administered by applying them directly to the affected part of the skin or by applying them in the form of a patch, plaster, poultice, or the like to the affected part, several times, e.g. once to thrice, per day. The number of applications may appropriately be increased or reduced depending upon the extent of the disease to be treated.

In the topical preparations of the present invention, a mixture of the cyclosporin solution in the organic solvent with the liquid monovalent alcohol-fatty acid ester and/or alkanol amine is contained in the oily substance in a homogeneously dispersed state. Hence, the topical preparations are so highly likely to infuse or penetrate through the skin that they can provide highly therapeutic effects upon autoimmune or allergic skin diseases merely by applying them to the affected part of the skin. Further, the topical preparations are only slightly irritative or extremely low in irritation to the skin so that they are highly safe.

The topical preparations according to the present invention are highly effective for the therapy of various dermal diseases such as atopic dermatitis, psoriasis, contact dermatitis, allergic contact dermatitis, alopecia, and the like. Further, they are effective for treating other dermal diseases, such as scald. The topical preparations can assist in grafting a skin piece to the site of skin grafting.

The present invention will be described more in detail by way of examples.

EXAMPLE 1

For a topical preparation, there were employed the following components:

Cyclosporin: 1% by weight
95% Ethanol: 3% by weight
Isopropyl myristate: 5% by weight
Olive oil: 48% by weight
Polyoxyethylene (5) glyceryl monostearate: 35% by weight
Finely divided silica (Aerosil 200): 8% by weight The topical preparation was formulated by mixing isopropyl myristate, polyoxyethylene (5) glyceryl monostearate and olive oil with stirring at 50° C. to give a homogenous solution to which a solution of cyclosporin in ethanol was added, and the resulting mixture heated to 30°-35° C. was mixed with the aerosil to give an ointment.

EXAMPLE 2

A topical preparation was prepared in substantially the same manner as in Example 1 using the following components:

Cyclosporin: 1% by weight
95% Ethanol: 5% by weight
Isopropyl myristate: 5% by weight
Olive oil: 47% by weight
Polyoxyethylene (5) glyceryl monostearate: 35% by weight
Finely divided silica (Aerosil 200): 7% by weight

EXAMPLE 3

A topical preparation was prepared in substantially the same manner as in Example 1 using the following components:

Cyclosporin: 2% by weight
95% Ethanol: 10% by weight
Isopropyl myristate: 5% by weight
Camellia oil: 44% by weight
Polyoxyethylene (5) glyceryl monostearate: 32% by weight
Finely divided silica (Aerosil 200): 7% by weight

EXAMPLE 4

After the skins of guinea pigs were sensitized with dinitrofluorobenzene (DNFB), DNFB was applied again, thereby causing a strong allergic reaction to emerge on the skins of the guinea pigs.

The efficacy of the topical preparations according to the present invention was examined using this experimental model.

Cyclophosphamide was intraperitoneally administered at the rate of 200 mg per kg three days before the sensitization of male Hartley guinea pigs, weighing from 40 grams to 500 grams, and 50 μl of a 10% DNFB solution in a 1:1 mixture of acetone and olive oil was applied to one earlobe of each of the guinea pigs. At day 8, a dose of 20 μl of 0.5% or 0.1% DNFB solution in a 4:1 mixture of acetone and olive oil was applied to the both sides of the depilated abdominal portions of the guinea pigs, whereby a contact dermal allergic reaction was induced.

After DNFB was then applied as an antigen to the corresponding sites of both abdominal portions, the topical preparations prepared in Example 1 (containing cyclosporin in the concentrations of 0.1%, 1% and 10%) were applied in the amount of 50 μl thereto. This application was repeated twice a day at an interval of 8 hours. The first application of each topical preparation was conducted immediately after the DNFB had been air dried.

The allergic reaction was evaluated at 24 hours, 48 hours and 72 hours after the application of the antigen in accordance with the following criteria: Rating 4=red swelling; rating 3=red coloration; rating 2=pink coloration; rating 1=a spot with pink coloration; and rating 0=no change. The values as shown in Table 1 below represent the mean value plus or minus the standard error (SE).

The statistical analysis was conducted with Student's t-test, and a significant difference was justified if the error rate was p<0.05.

The application of the 0.5% DNFB solution caused the strongest allergic reaction over the time range from 24 hours to 48 hours after the application. The 0.1% cyclosporin ointment suppressed the allergic reaction to a considerable extent with no significant difference. On the other hand, the ointment containing 1% cyclosporin reduced the allergic reaction to a remarkable extent at 24 hours with the significant difference of p<0.01. Even at 48 hours and 72 hours, the allergic reaction was suppressed with the significant difference. Further, the ointment containing 10% cyclosporin demonstrated significant suppression of the allergic reaction, like the 1% cyclosporin ointment. As a control, the ointment base alone did not suppress the allergic reaction at all. The results are shown in Table 1 below.

TABLE 1

| Test Samples | | | | |
|---|---|---|---|---|
| Cyclosporin (%) | No. of guinea pigs | 24 hours | 48 hours | 72 hours |
| 0 | 9 | 3.4 ± 0.2 | 3.4 ± 0.2 | 2.7 ± 0.2 |
| 0.1 | 9 | 2.4 ± 0.3 | 2.7 ± 0.3 | 1.8 ± 0.3 |
| 1.0 | 9 | 0.7 ± 0.3** | 1.0 ± 0.3** | 1.0 ± 0.3** |
| 0 | 4 | 3.3 ± 0.3 | 3.3 ± 0.3 | 3.3 ± 0.3 |
| 10 | 4 | 0.8 ± 0.5* | 1.0 ± 0.6* | 1.0 ± 0.5 |

*p < 0.05
**p < 0.01

When the 0.1% DNFB solution was applied, the strongest allergic reaction appeared at 48 hours after the application. The 0.1% cyclosporin topical preparation suppressed the allergic reaction to a remarkable extent with the significant difference of p<0.01. The allergic reaction was likewise suppressed even at 48 hours and 72 hours. On the other hand, the topical preparations containing 1% and 10% cyclosporin showed reduction in the allergic reaction with the significant difference, like the topical preparation containing 0.1% cyclosporin. As a control, the ointment base alone did not suppress the allergic reaction at all. The results are shown in Table 2 below.

TABLE 2

| Test Samples | | | | |
|---|---|---|---|---|
| Cyclosporin (%) | No. of guinea pigs | 24 hours | 48 hours | 72 hours |
| 0 | 8 | 2.1 ± 0.3 | 3.1 ± 0.2 | 2.5 ± 0.2 |
| 0.1 | 8 | 0.3 ± 0.2** | 1.0 ± 0.2** | 0.8 ± 0.2** |
| 1.0 | 8 | 0.1 ± 0.1** | 0.4 ± 0.3** | 0.1 ± 0.1** |
| 0 | 4 | 2.0 ± 0.4 | 3.0 ± 0 | 2.3 ± 0.3 |
| 10 | 4 | 0 ± 0* | 0.5 ± 0.3* | 0.3 ± 0.3* |

*p < 0.05
**p < 0.01

EXAMPLE 5

Case 1:

A male patient, 27 years old, had been affected with atopic dermatitis since age 22 although a temporary remission had been gained at age 8 from the atopic dermatitis since age 3. Various steroidal ointments had been applied but were found ineffective. With the 10% cyclosporin ointment according to the present invention, an itch on his skin disappeared four to five hours after the application of the ointment and the lichenized erythra peculiar in the atopic dermatitis disappeared completely at day 3 after its application when the ointment was applied twice per day.

Case 2:

A male child, 6 years old, had been affected with atopic dermatitis since age 3 and was treated with Azeptin, Zaditen, and Rizaben as well as ointments such as Rinderon V, Locorten and Methaderm; however, no effect was recognized. The application of a 5% cyclosporin ointment according to the present invention eliminated itch to his skin within 5 hours after the topical administration and the itch, erythema and wet erosion of the affected part had disappeared within 24 hours after the application.

Case 3:

A male patient, 52 years old, affected with psoriatic arthritis, was treated with 1% cyclosporin ointment according to the present invention, applied to the wet erythema with a clear borderline and to the scales on the surface thereof. The 1% cyclosporin ointment improved the Auspitz phenomenon within 24 hours after the application with the erythema disappearing at day 3 from the application of the ointment.

EXAMPLE 6

In order to demonstrate the efficacy of the topical preparations according to the present invention, the ointments were prepared from the components as shown in Table 3 below and the efficacy thereof was evaluated in substantially the same manner as in Example 4. The evaluation results are shown in Table 3 below.

TABLE 3

| | Contents (% by weight) Experiment Nos. | | | | | | |
|---|---|---|---|---|---|---|---|
| Components | 1* | 2* | 3 | 4 | 5 | 6 | 7 |
| Cyclosporin | 5 | 5 | 5 | 5 | 10 | 5 | 10 |
| 95% Ethanol | 0 | 0 | 2 | 5 | 10 | 5 | 10 |
| Isopropyl myristate | 5 | 5 | 5 | 5 | 5 | 0 | 3 |
| Olive oil | 48 | 48 | 48 | 45 | 35 | 36 | 36 |

TABLE 3-continued

| Components | Contents (% by weight) Experiment Nos. | | | | | | |
|---|---|---|---|---|---|---|---|
| | 1* | 2* | 3 | 4 | 5 | 6 | 7 |
| Polyoxyethylene glycol monostearate | 35 | 35 | 35 | 35 | 35 | 36 | 36 |
| Aerosil | 5 | 7 | 5 | 5 | 5 | 6 | 6 |
| Triethanol amine | 2 | 0 | 0 | 0 | 0 | 3 | 2 |
| Efficacy | None | None | Yes | Yes | Yes | Yes | Yes |

*Comparative Examples

Comparative Examples

The following topical preparations containing cyclosporin were prepared for comparative purposes in a conventional manner:
  i. A caster oil suspension containing 5% by weight of cyclosporin;
  ii. A suspension of 5% by weight of cyclosporin in castor oil containing 20% by weight of propylene glycol; and
  iii. An ointment containing 10% by weight of cyclosporin, 43% by weight of olive oil, 10% by weight of ethanol, 7% by weight of polyoxyethylene (5) oleate, and 30% by weight of silicon dioxide in colloidal state.

The topical preparations prepared in the manner as described hereinabove were evaluated for their pharmaceutical efficacy in substantially the same manner as in Example 4; however, none of them were found significantly effective.

EXAMPLE 7

A topical preparation was prepared from the components as follows:
  Cyclosporin: 5% by weight
  95% Ethanol: 2% by weight
  Isopropyl myristate: 7% by weight
  Camellia oil: 40% by weight
  Polyoxyethylene (5) glyceryl monostearate: 41% by weight
  Finely divided silica (Aerosil 200): 5% by weight The topical preparation was formulated in substantially the same manner as in Example 1.

EXAMPLE 8

A topical preparation was prepared in substantially the same manner as in Example 1 using the components as follows:
  Cyclosporin: 5% by weight
  95% Ethanol: 5% by weight
  Isopropyl myristate: 5% by weight
  Camellia oil: 39% by weight
  Polyoxyethylene (5) glyceryl monostearate: 39% by weight
  Finely divided silica (Aerosil 200): 5% by weight

EXAMPLE 9

After each of the topical preparations prepared in Examples 7 and 8 were stored in a closed state for 6 months at relative temperature of 75% and temperature of 40° C., the content of cyclosporin within the topical preparation was measured. As a result, it was found that no substantial changes were observed between before or after storage. Thus, it is confirmed that cyclosporin is sustained in a stable state for a long period of time.

EXAMPLE 10

A mixture (A) was prepared by dissolving 50 grams of cyclosporin, 70 grams of 2-octyl dodecanol, 30 grams of isopropyl myristate, 20 grams of isotridecyl myristate, 10 grams of polyoxyethylene sorbitan monooleate (20), 50 grams of polyoxyethylene glyceryl monostearate (5), 10 grams of sorbitan monostearate, 30 grams of cetanol, 40 grams of sebacate and 30 grams of olive oil at 80° C. On the other hand, a mixture (B) was prepared by adding 30 grams of propylene glycol, 20 grams of diisopropanol amine, 2 grams of carboxyvinyl polymer, 1 gram of methyl p-hydroxybenoate, and 1 gram of propyl p-hydroxybenzoate to 596 ml of sterilized water and heating the mixture to approximately 82° C. As the two mixtures reached the predetermined temperatures, the mixture A was gradually added with vigorous stirring to the mixture B, thereby producing an emulsion. After the addition was completed, the heating was ceased and the temperature of the emulsion was stirred and cooled down to 60°–55°. Then, sterilized water was added to make the total volume of the mixture 1 kg. The whole mixture was allowed to stand and defoam, and then filled in a vessel.

In the above composition, polyoxyethylenel glyceryl monostearate (5) can be replaced by 2.0% by weight of polyoxyethylene (2) cetyl ether; sorbitan monostearate can be replaced by squalane SK; and cetanol can be replaced by behenyl alcohol. Further, the total volume of the sterilized water used for the mixture (B) can be replaced by liquid paraffin.

EXAMPLE 11

A mixture (A) was prepared by dissolving 50 grams of cyclosporin, 50 grams of ethanol, 50 grams of isopropyl myristate, 50 grams of polyethylene glycol (400), 30 grams of dithyl sebacate, 80 grams of olive oil, 30 grams of polyoxyethylene monostearate (5), 30 grams of polyethylene glycol monostearate (40), and 20 grams of sorbitan monostearate at elevated temperature. On the other hand, a mixture (B) was prepared by dissolving 50 grams of polyethylene glycol, 20 grams of diisopropanol amine, 10 grams of carboxyvinyl polymer, 1 gram of methyl p-hydroxybenoate, and 1 gram of propyl phydroxybenzoate in 528 ml of sterilized water at elevated temperature. The mixture A was gradually added with vigorous stirring to the mixture B, thereby producing an emulsion. After the addition was completed, the total volume of the mixture was increased to make 1 kg by adding sterilized water to the mixture.

In the above composition, ethanol can be replaced by behenyl alcohol, and diisopropanol amine can be replaced by triethanol amine.

EXAMPLE 12

A mixture (A) was prepared by dissolving 50 grams of cyclosporin, 10 grams of octyl alcohol, 50 grams of olive oil, 30 grams of isopropyl myristate, 25 grams of isotridecyl myristate, 20 grams of polyoxyethylene sorbitan monooleate (20), 60 grams of polyoxyethylenel glyceryl monostearate (5), 20 grams of sorbitan stearate, 30 grams of cetanol, 25 grams of stearic acid, and 35 grams of diethyl sebacate at 80° C. On the other hand, a mixture (B) was prepared by adding and dissolving 20 grams of polyethylene glycol, 20 grams of diisopropanol amine, 2 grams of carboxyvinyl polymer, 0.5 gram of methyl p-hydroxybenzoate, and 0.5 gram of propyl phydroxybenzoate to and in approximately 400 ml of sterilized water by heating the mixture to 82° C. or higher. The mixture 8 was gradually added with vigorous stirring to the mixture A, thereby producing an emulsion. After the addition was completed, the heating was ceased and sterilized water was added at 80° C. to the resulting mixture with stirring at room temperature, thereby increasing the total volume of the mixture to make 1 kg. The whole mixture was allowed to stand and to defoam; then the ointment in cream form was filled into a container.

In the above composition, isopropyl myristate can be replaced by isopropyl palmitate.

EXAMPLE 13

A mixture (A) was prepared by dissolving 50 grams of cyclosporin, 30 grams of bees wax, 80 grams of 2,6-dimethyl-4-heptanol, 30 grams of olive oil, 40 grams of isotridecyl myristate, 20 grams of polyoxyethylene sorbitol hexastearate (20), 60 grams of polyoxyethylenel glyceryl monostearate (5), 20 grams of polyoxyethylene (60) hardened castor oil, 40 grams of cetostearyl alcohol, and 40 grams of diethyl sebacate at 80° C. On the other hand, a mixture (B) was prepared by adding and dissolving 30 grams of polyethylene glycol, 20 grams of diisopropanol amine, 2 grams of carboxyvinyl polymer, 0.5 gram of methyl p-hydroxybenzoate, and 0.5 gram of propyl p-hydroxybenzoate to and in 510 ml of sterilized water by heating the mixture to 82° C. or higher. The mixture (B) was gradually added with vigorous stirring to the mixture (A) maintained at 80° C. After the addition was completed, the heating was ceased and the mixture was cooled down to 60°-55° C. with stirring. Then, sterilized water heated to 80° C. was added to the resulting mixture with stirring at room temperature, thereby increasing the total volume of the mixture to make 1 kg. The whole mixture was allowed to stand and to defoam: then the resulting mixture was filled into a container.

In the above composition, the bees wax can be replaced by polyoxyethylene lanolyl alcohol or a bees wax derivative; isotridecyl myristate can be replaced by 0.2% by weight of silicone oil; polyoxyethylenel sorbitan oleate (20) can be replaced by polyoxyethylenel sorbitan fatty acid ester; sorbitan monostearate can be replaced by squalane SK; and sterilized water can be replaced by liquid paraffin.

EXAMPLE 14

A mixture (A) was prepared by mixing 50 grams of cyclosporin, 80 grams of propylene glycol monocaprylate, 30 grams of isopropyl myristate, 30 grams of PEG monostearate (25EO), 30 grams of polyethylene glycol, 20 grams of isotridecyl myristate, 20 grams of cetanol, 50 grams of olive oil, 80 grams of whale wax, 30 grams of sorbitan monostearate, 30 grams of polyoxyethylene glyceryl monostearate (5), 30 grams of stearic acid, 20 grams of diisopropanol amine, and 40 grams of diethyl sebacate and heating the resulting mixture at 80° C. On the other hand, a mixture (B) was prepared by adding 30 grams of propylene glycol, 15 grams of diisopropanol amine, 2 grams of carboxyvinyl polymer, 0.5 gram of methyl p-hydroxybenzoate, and 0.5 gram of propyl p-hydroxybenzoate to approximately 400 ml of sterilized water and heating the resulting mixture to 82° C. or higher. The mixture (B) was gradually added with vigorous stirring to the mixture (A) maintained at 80° C. or higher. After the addition was completed, the heating was ceased and the mixture was stirred to cool the temperature of the mixture to 60°-55° C., followed by adding sterilized water heated at 80° C. to the resulting mixture to increase the total volume of the mixture to make 1 kg. The whole mixture was allowed to stand and to defoam; then the resulting mixture was filled in a container.

EXAMPLE 15

A mixture (A) was prepared by mixing 50 grams of cyclosporin, 70 grams of 2-octyl dodecanol, 30 grams of isoprene glycol, 40 grams of diethyl sebacate, 30 grams of isopropyl myristate, 30 grams of isotridecyl myristate, 60 grams of whale wax, 30 grams of cetanol, 40 grams of stearic acid, 20 grams of POE (5) glyceryl monostearate, 20 grams of PEG monostearate (40EO), 10 grams of sorbitan monostearate, 50 grams of olive oil, and 1 gram of propylparaben and heating the mixture to 80° C. On the other hand, a mixture (B) was prepared by adding 30 grams of butylene glycol, 20 grams of diiso-propanol amine, and 1 gram of methylparaben to 460 ml of sterilized water and heating the resulting mixture to 82° C. or higher. The mixture (B) was gradually added with vigorous stirring to the mixture (A) maintained at 80° C. or higher. After the addition was completed, the heating was ceased and the temperature of the mixture was cooled down to 60°-55° C. with stirring. Then, sterilized water heated at 80° C. was added to the resulting mixture, thereby increasing the total volume of the mixture to 1 kg. The whole mixture was allowed to stand and to defoam; then the resulting mixture was filled in a container.

EXAMPLE 16

A solution of 50 grams of cyclosporin in 80 grams of 2-octyl dodecanol was added to a warmed mixture of 40 grams of isopropyl myristate, 370 grams of olive oil, 378 grams of polyoxyethylene (5) glyceryl monostearate, 2 grams of polyoxyethylene (9) lauryl ether, and 10 grams of sorbitan monostearate, and 70 grams of aerosil was added to the resulting mixture, thereby yielding a topical preparation of a non-emulsion type.

EXAMPLE 17

The efficacy of the creamy ointment containing cyclosporin, prepared in substantially the same manner as in Example 15, was confirmed by applying it to the transplant of the skin sections of mice.

The skin sections of 10 male CBA mice of 5 weeks were transplanted to male C3H/HeN mice of the same week. To the transplanted sites and the portions surrounding them was applied approximately 0.1 gram of the ointment prepared in Example 12 two times per day until the transplanted sections eventually fell off. The results are shown in Table 4 below.

TABLE 4

| Cyclosporin (%) | Period of Transplantation* | Effect of Extension | Significant Difference** |
|---|---|---|---|
| 5.0 | >60 | >397 | p < 0.001 |
| 1.0 | 31.3 ± 1.43 | 207 | p < 0.001 |
| 0.0 (as control) | 15.1 ± 0.78 | 100 | — |

*mean value ± SE
**Student's t-test

For a control group in which a cream without cyclosporin was applied, the transplanted skin specimens fell off at an average after transplantation of 12.7 days, while a group in which a cream containing 5% cyclosporin was applied had all the transplanted skin sections grow for 60 days or longer. For a group in which a cream containing 1% cyclosporin was applied, the period of transplantation for which the transplanted skin sections grew was extended with significant difference to a mean of 31.3 days.

EXAMPLE 18

Eight Hartley male guinea pigs weighing approximately 300 grams were intraperitoneally administered 150 mg/kg of cyclophosphamide, and 50 μl of a 10% dinitroflurobenzene (DNFB) solution was applied to one earlobe of each guinea pig three days after the intraperitoneal administration. The DNFB solution was prepared by dissolving the predetermined amount of the DNFB in a 1:1 mixture of acetone with olive oil. After 8 days, the hairs on both the abdominal parts were cut off and 20 μl of a 0.1% DNFB solution was applied to the depilated abdominal parts of the guinea pigs to induce contact dermal allergy. Immediately thereafter, the cyclosporin ointment prepared in substantially the same manner as in Example 15 was applied to the parts to which the DNFB solution had been applied, followed by applying the cyclosporin ointment thereto in 8 hours. To a control group, the base used in Example 15 without cyclosporin was applied in accordance with the same schedule as described hereinabove.

The allergic reaction was determined at 24 hours, 48 hours and 72 hours after the application of the DNFB solution as the antigen, and the rating was: 4 = red swelling; 3 = red coloration; 2 = inflammation causing the skin to turn pink; 1 = inflammation causing the skin to turn pale pink; and 0 = no change. The results are shown in Table 5 below.

TABLE 5

| Cyclosporin (%) | Severity of Dermal Reaction (mean value + SE) | | |
|---|---|---|---|
| | 24 hours | 48 hours | 72 hours |
| 1.0 | 0.0 ± 0.0** | 0.3 ± 0.2** | 0.1 ± 0.1** |
| 0.1 | 0.3 ± 0.3** | 0.9 ± 0.2** | 0.7 ± 0.3** |
| 0.0 (control) | 2.2 ± 0.3** | 3.1 ± 0.2** | 2.4 ± 0.2** |

**$p < 0.001$ in Student's t-test

In these experiments, the strongest allergic reaction was induced over the range extending from 24 hours to 48 hours after the application of the DNFB solution. The ointment containing 1.0% cyclosporin strongly suppressed the allergic reaction and the ointment containing 0.1% cyclosporin suppressed the allergic reaction with significant difference.

What is claimed is:

1. A topical preparation comprising: (a) approximately 0.1 to 10% by weight cyclosporin; (b) an organic solvent in which said cyclosporin is dissolved; and (c) approximately 1% to 15% by weight of a skin penetration enhancer, said skin penetration enhancer being at least one member selected from the group consisting of alkanolamines and monovalent alcohol esters of myristic acid, adipic acid and sebacic acid, said (c) being liquid at 25° C.

2. A topical preparation as claimed in claim 1, wherein said organic solvent is aliphatic alcohol which is liquid at 25° C.

3. A topical preparation as claimed in claim 2, wherein said aliphatic alcohol is a lower alcohol.

4. A topical preparation as claimed in claim 3, wherein said lower alcohol is ethanol.

5. A topical preparation as claimed in claim 2, wherein said aliphatic alcohol is a higher alcohol having a branched chain and at least 8 carbon atoms.

6. A topical preparation as claimed in claim 5, wherein said higher alcohol is 2-octyldodecanol.

7. A topical preparation as claimed in claim 1, wherein said organic solvent is a monoester of a fatty acid with a polyhydric alcohol.

8. A topical preparation as claimed in claim 7, wherein said monoester is propyleneglycol monocaprate or propylene glycol monocaprylate.

9. A topical preparation as claimed in claim 1, wherein said organic solvent is present in an amount ranging from approximately 0.5 part to 10 parts by weight per part by weight of said cyclosporin.

10. A topical preparation as claimed in claim 1 wherein said preparation is an emulsion.

11. A topical preparation as claimed in any one of claims 1, 2, 3, 4, 5, 6, 7, 8 or 9 further comprising a vegetable oil.

12. A topical preparation as claimed in any one of claims 1, 2, 3, 4, 5, 6, 7, 8 or 9 further comprising a surfactant.

13. A topical preparation as claimed in any one of claims 1, 2, 3, 4, 5, 6, 7, 8 or 9 further comprising a filler.

14. A topical preparation as claimed in any one of claims 1, 2, 3, 4, 5, 6, 7, 8 or 9 further comprising at least one of an alkylene glycol and a polyalkylene glycol.

15. A topical preparation comprising: (a) approximately 0.1% to 10% by weight of cycliosporin; (b) approximately 2% to 15% by weight of lower alcohol; and (c) approximately 1% to 15% by weight of a skin penetration enhancer, said skin penetration enhancer being at least one member selected from the group consisting of alkanolamines and monovalent alcohol esters of myristic acid, adipic acid and sebacic acid.

16. A topical preparation as claimed in claim 15, wherein said lower alcohol is at least one member selected from the group consisting of ethanol, isopropanol, propanol and isobutanol.

17. A topical preparation as claimed in claim 15 wherein said preparation is an emulsion.

18. A topical preparation as claimed in claim 15, further comprising from approximately 5% to 10% by weight of a filler.

19. A topical preparation comprising 0.1% to 10% by weight of cyclosporin; 2% to 15% by weight of ethanol; 1% to 15% by weight of isopropyl myristate; 35% to 60% by weight of olive oil or camellia oil; 20% to 40% by weight of a surfactant; and 5% to 10% by weight of silica.

* * * * *